(12) United States Patent
Yoshimura

(10) Patent No.: US 11,690,600 B2
(45) Date of Patent: Jul. 4, 2023

(54) ULTRASOUND OBSERVATION APPARATUS, OPERATION METHOD OF ULTRASOUND OBSERVATION APPARATUS, AND COMPUTER-READABLE RECORDING MEDIUM

(71) Applicant: OLYMPUS CORPORATION, Tokyo (JP)

(72) Inventor: Takehiro Yoshimura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 1141 days.

(21) Appl. No.: 15/862,893

(22) Filed: Jan. 5, 2018

(65) Prior Publication Data

US 2018/0125457 A1 May 10, 2018

Related U.S. Application Data

(63) Continuation of application No. PCT/JP2016/069901, filed on Jul. 5, 2016.

(30) Foreign Application Priority Data

Jul. 9, 2015 (JP) ................................ 2015-137864

(51) Int. Cl.
*A61B 8/08* (2006.01)
*A61B 8/12* (2006.01)
(Continued)

(52) U.S. Cl.
CPC .............. *A61B 8/5207* (2013.01); *A61B 8/12* (2013.01); *A61B 8/463* (2013.01); *A61B 8/485* (2013.01);
(Continued)

(58) Field of Classification Search
CPC ......... A61B 8/5207; A61B 8/12; A61B 8/463; A61B 8/485; A61B 8/585; A61B 8/488; A61B 8/5223; G06T 11/008
See application file for complete search history.

(56) References Cited

U.S. PATENT DOCUMENTS 6,328,693 B1 * 12/2001 Miyatake ............. A61B 8/5238
600/443
2007/0160275 A1 7/2007 Sathyanarayana
(Continued)

FOREIGN PATENT DOCUMENTS

JP 2007-268148 A 10/2007
JP 2007268148 A * 10/2007
(Continued)

OTHER PUBLICATIONS

Extended Supplementary European Search Report dated Sep. 19, 2019 in European Patent Application No. 16 82 1402.1.
(Continued)

*Primary Examiner* — Keith M Raymond
*Assistant Examiner* — Sean A Frith
(74) *Attorney, Agent, or Firm* — Scully, Scott, Murphy & Presser, P.C.

(57) ABSTRACT

An ultrasound observation apparatus includes: a B-mode image generation unit; a region selection information input unit; a region-of-interest setting unit configured to set a region of interest of an ultrasound image to be subjected to processing suitable for an operation mode selected, in accordance with the input, from a plurality of operation modes for detecting a selected one of a plurality of pieces of characteristic biological information, by calculation using a region-of-interest setting method previously associated with the operation mode, based on a desired region selected in the region selection information; and a mode image composition unit configured to generate a mode composite image in
(Continued)

| MODE \ ENDOSCOPE TYPE | RADIAL A | RADIAL B | ... | CONVEX A | CONVEX B | ... |
|---|---|---|---|---|---|---|
| FLOW | W1 | W11 | ... | W21 | W31 | ... |
| ELASTO | W2 | W12 | ... | W22 | W32 | ... |
| CONTRAST MEDIUM | W3 | W13 | ... | W23 | W33 | ... |
| ⋮ | ⋮ | ⋮ | ⋮ | ⋮ | ⋮ | ⋮ |

T1 which an operation mode image presented in two dimensions additional information obtained by performing processing suitable for the operation mode selected in accordance with the input on the region of interest is superimposed on a B-mode image generated by the B-mode image generation unit.

10 Claims, 18 Drawing Sheets

(51) Int. Cl.
*A61B 8/00* (2006.01)
*G06T 11/00* (2006.01)

(52) U.S. Cl.
CPC ............ *A61B 8/585* (2013.01); *G06T 11/008* (2013.01); *A61B 8/488* (2013.01); *A61B 8/5223* (2013.01)

(56) References Cited

U.S. PATENT DOCUMENTS

| | | | |
|---|---|---|---|
| 2012/0189178 A1 | 7/2012 | Seong | |
| 2012/0283567 A1* | 11/2012 | Chono | A61B 8/5284 600/447 |
| 2012/0330557 A1* | 12/2012 | Zhang | A61B 6/503 702/19 |
| 2014/0039316 A1* | 2/2014 | Ichioka | A61B 8/483 600/439 |
| 2014/0163373 A1* | 6/2014 | Noguchi | A61B 8/12 600/443 |
| 2015/0005633 A1 | 1/2015 | Kanayama et al. | |
| 2015/0094569 A1* | 4/2015 | Ohuchi | A61B 8/0841 600/424 |
| 2015/0148674 A1* | 5/2015 | Park | A61B 8/085 600/438 |
| 2015/0196283 A1* | 7/2015 | Yamamoto | A61B 8/0825 600/437 |
| 2015/0245817 A1* | 9/2015 | Stone | A61B 10/02 600/443 |
| 2015/0250446 A1* | 9/2015 | Kanayama | A61B 8/468 600/438 |
| 2016/0310110 A1* | 10/2016 | Dodd | A61B 8/54 |

FOREIGN PATENT DOCUMENTS

| | | |
|---|---|---|
| JP | 2009-112436 A | 5/2009 |
| JP | 2012-155723 A | 8/2012 |
| JP | 2014050631 A * | 3/2014 |
| JP | 2015-009040 A | 1/2015 |
| WO | 01/01864 A1 | 1/2001 |

OTHER PUBLICATIONS

International Search Report dated Aug. 2, 2016 issued in PCT/JP2016/069901.

* cited by examiner

ULTRASOUND OBSERVATION APPARATUS, OPERATION METHOD OF ULTRASOUND OBSERVATION APPARATUS, AND COMPUTER-READABLE RECORDING MEDIUM

CROSS REFERENCES TO RELATED APPLICATIONS

This application is a continuation of PCT international application Ser. No. PCT/JP2016/069901, filed on Jul. 5, 2016 which designates the United States, incorporated herein by reference, and which claims the benefit of priority from Japanese Patent Application No. 2015-137864, filed on Jul. 9, 2015, incorporated herein by reference.

BACKGROUND

The present disclosure relates to an ultrasound observation apparatus, an operation method of an ultrasound observation apparatus, and a computer-readable recording medium.

Ultrasound waves are sometimes used to observe characteristics of living tissue or materials to be observed. Specifically, by transmitting ultrasound waves to an observation target, and performing predetermined signal processing on ultrasound echoes reflected by the observation target, information on characteristics of the observation target is obtained.

An ultrasound endoscope provided with an ultrasound transducer at the distal end of its insertion portion is used for diagnosing living tissue or the like in a body to which ultrasound waves are applied. After inserting the insertion portion into a body, an operator such as a doctor operates an operation unit at hand, thereby causing the ultrasound transducer to acquire ultrasound echoes. Based on information in accordance with the ultrasound echoes (an ultrasound image), the operator makes a diagnosis. When it is desired to diagnose in more detail or when it is desired to improve the accuracy of result comprehensively based on diagnosis from another viewpoint, an ultrasound image is displayed in various operation modes such as a flow-mode, an elasto-mode, and a contrast medium-mode in an ultrasound observation system. Specifically, a region of interest is set on a basic B-mode image, and an operation mode image in which additional information obtained by performing processing such as an operation suitable for a set operation mode on the region of interest is presented in two dimensions is generated and superimposed on the B-mode image, and displayed on a monitor.

In the related art, configurations have been proposed in which a region of interest in an ultrasound image is set using a pointing device such as a dial ring, a track ball, or a mouse (see, for example, JP 2009-112436 A). In JP 2009-112436 A combinations of a plurality of regions different in size and position are set as candidate regions for a region of interest. An operator operates a pointing device to display candidate regions for a region of interest, then operates the pointing device again to select a candidate region suitable for an operation mode, and thereby sets a region of interest.

SUMMARY

An ultrasound observation apparatus according to one aspect of the present disclosure transmits ultrasound waves to a subject that is an observation target, and generates ultrasound images displayed on a display unit, based on an ultrasound signal acquired by an ultrasound endoscope receiving the ultrasound waves reflected by the subject, the apparatus including: a B-mode image generation unit configured to generate a B-mode image in which amplitude of the reflected ultrasound waves is converted into luminance by processing the ultrasound signal and presented in two dimensions; a region selection information input unit configured to receive input of region selection information selecting a desired region from the ultrasound images displayed on the display unit; a region-of-interest setting unit configured to set a region of interest of the ultrasound image that is a region to be subjected to processing suitable for an operation mode selected, in accordance with the input, from a plurality of operation modes for detecting a selected one of a plurality of pieces of characteristic biological information, by calculation using a region-of-interest setting method previously associated with the operation mode, based on the desired region selected in the region selection information; and a mode image composition unit configured to generate a mode composite image in which an operation mode image presented in two dimensions additional information obtained by performing processing suitable for the operation mode selected in accordance with the input on the region of interest is superimposed on the B-mode image generated by the B-mode image generation unit.

The above and other features, advantages and technical and industrial significance of this invention will be better understood by reading the following detailed description of presently preferred embodiments of the invention, when considered in connection with the accompanying drawings.

DETAILED DESCRIPTION

Figure 1:
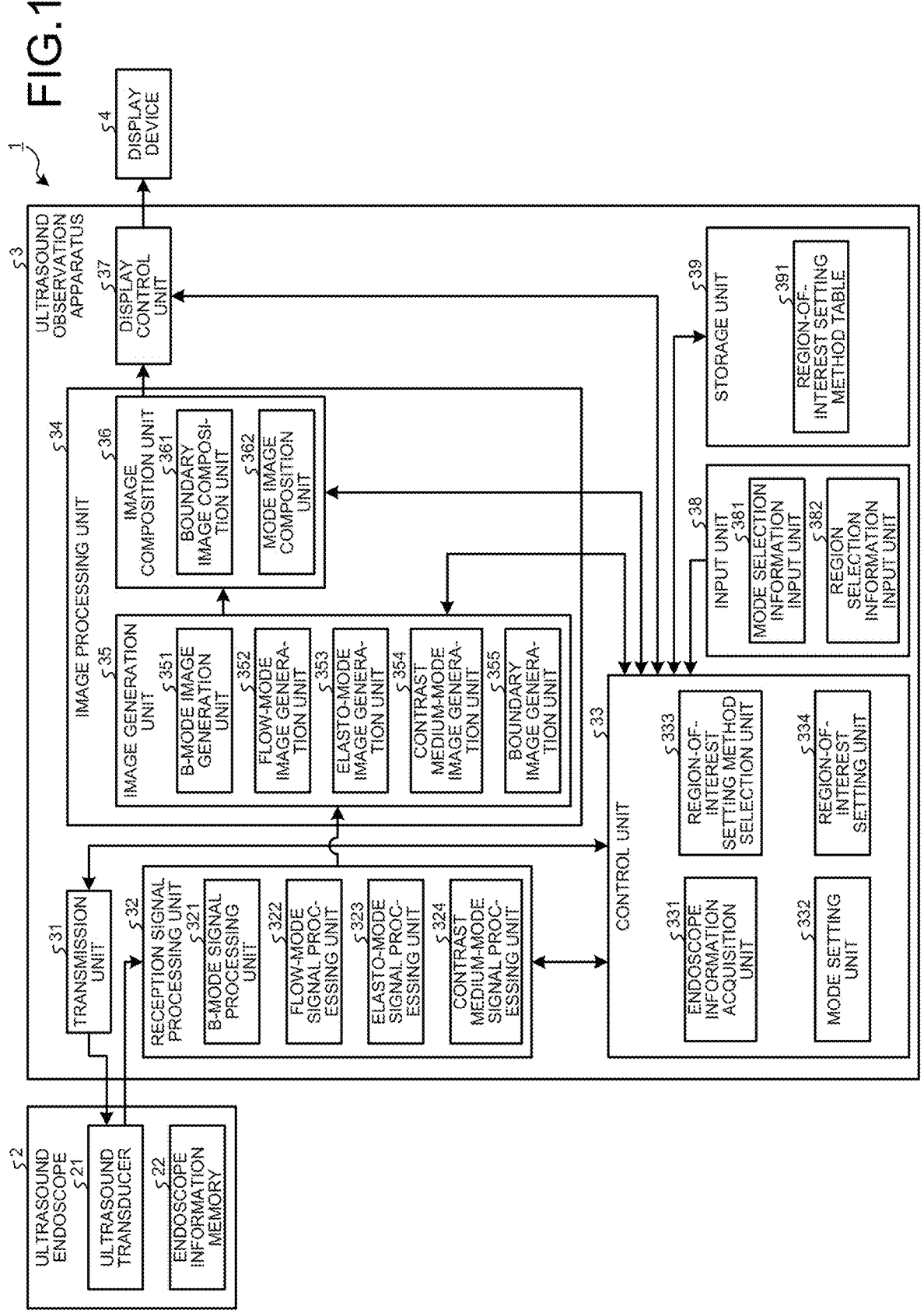
FIG. 1 is a block diagram illustrating a configuration of an ultrasound observation system according to a first embodiment.

Hereinafter, embodiments will be described with reference to the accompanying drawings. In the following description, an ultrasound observation system for generating an ultrasound image based on ultrasound echoes is exemplified, but the present disclosure is not limited by these embodiments. The same components will be described with the same reference numerals.

First Embodiment

FIG. 1 is a block diagram illustrating a configuration of an ultrasound observation system according to a first embodiment. An ultrasound observation system 1 illustrated in FIG. 1 is a system for observing an observation target using ultrasound waves. The ultrasound observation system 1 includes an ultrasound endoscope 2 for transmitting ultrasound waves to a subject as an observation target and receiving the ultrasound waves reflected by the subject, an ultrasound observation apparatus 3 for generating an ultrasound image to be displayed on a display device 4, based on an ultrasound signal acquired by the ultrasound endoscope 2, and the display device 4 connected to the ultrasound observation apparatus 3 for displaying an image generated by the ultrasound observation apparatus 3.

The ultrasound endoscope 2 includes an ultrasound transducer 21 provided at a distal end portion thereof and an endoscope information memory 22. The ultrasound transducer 21 converts an electrical pulse signal received from the ultrasound observation apparatus 3 into ultrasound pulses (acoustic pulses) and irradiates the subject with the ultrasound pulses, and converts ultrasound echoes reflected by the subject into an electrical echo signal (ultrasound signal) representing the ultrasound echoes in a changing voltage and outputs it. The ultrasound transducer 21 may be a radial transducer, a convex transducer, or a linear transducer. The ultrasound endoscope 2 may mechanically scan the ultrasound transducer 21, or may have, as the ultrasound transducer 21, a plurality of elements provided in an array to electronically scan the ultrasound transducer 21 by electronically switching elements related to transmission or reception or delaying transmission or reception of each element. The endoscope information memory 22 stores various kinds of information including an ID for identification that is identification information on the ultrasound endoscope 2. Based on the identification information stored in the endoscope information memory 22, the ultrasound observation apparatus 3 may determine what generation the ultrasound endoscope 2 is in, and which type the ultrasound endoscope 2 is of, a radial type having a radial transducer, a convex type having a convex transducer and capable of protruding a puncture needle through a distal end opening, a linear type having a linear transducer, or the like.

The ultrasound endoscope 2 usually has an imaging optical system and an imaging device, and may be inserted into the digestive tract (esophagus, stomach, duodenum, and large intestine) or the respiratory tract (tracheae and bronchi) of the subject to image the digestive tract, the respiratory tract, or the surrounding organs (pancreas, gallbladder, bile duct, biliary tract, lymph nodes, mediastina, blood vessels, etc.). In addition, the ultrasound endoscope 2 has a light guide for guiding illumination light to be emitted to the subject at the time of imaging. The light guide has a distal end portion reaching the distal end of the insertion portion of the ultrasound endoscope 2 to be inserted into the subject, and a proximal end portion connected to a light source device that generates illumination light.

The ultrasound observation apparatus 3 includes a transmission unit 31, a reception signal processing unit 32, a control unit 33, an image processing unit 34, a display control unit 37, an input unit 38, and a storage unit 39.

The transmission unit 31 is electrically connected to the ultrasound endoscope 2, and transmits a transmission signal (pulse signal) composed of high-voltage pulses to the ultrasound transducer 21, based on a predetermined waveform and transmission timing. The frequency band of a pulse signal transmitted by the transmission unit 31 is preferably set to a wide band that substantially covers a linear response frequency band of the electroacoustic conversion of a pulse signal into ultrasound pulses in the ultrasound transducer 21. The transmission unit 31 transmits various control signals output from the control unit 33 to the ultrasound endoscope 2.

The reception signal processing unit 32 is electrically connected to the ultrasound endoscope 2, receives an echo signal (ultrasound signal) that is an electrical reception signal from the ultrasound transducer 21, and processes the received echo signal to generate data of a digital radio-frequency (RF) signal (hereinafter referred to as RF data). The reception signal processing unit 32 performs filtering processing, amplification processing, phase conversion processing, delay correction processing, synthesis processing, logarithmic conversion processing, Fourier transform processing, and the like on the RF data, and outputs the processed RF data to the image processing unit 34. The reception signal processing unit 32 receives the identification information including the ID for identification from the endoscope information memory 22 of the ultrasound endoscope 2, and outputs it to the control unit 33. The reception signal processing unit 32 includes a B-mode signal processing unit 321 for processing an echo signal for generating a B-mode image, a flow-mode signal processing unit 322 for processing an echo signal for generating a flow-mode image, an elasto-mode signal processing unit 323 for processing an echo signal for generating an elasto-mode image, and a contrast medium-mode signal processing unit 324 for processing an echo signal for generating a contrast medium-mode image.

The control unit 33 controls the entire ultrasound observation system 1. The control unit 33 is implemented using a CPU, various arithmetic circuits, or the like having arithmetic and control functions. The control unit 33 reads information stored by the storage unit 39 from the storage unit 39, executes various kinds of arithmetic processing related to an operation method of the ultrasound observation apparatus 3, and thereby centrally controls the ultrasound observation apparatus 3. The control unit 33 may be configured using a CPU or the like shared by the image processing unit 34. The control unit 33 includes an endoscope information acquisition unit 331, a mode setting unit 332, a region-of-interest setting method selection unit 333, and a region-of-interest setting unit 334. A region of interest is a region set on a B-mode image that is an ultrasound image to be described later, and is a region to be subjected to processing suitable for the operation mode. For a region of interest, a predetermined region is set as default and is optimized according to the operation mode in the region-of-interest setting unit 334 to be described later.

The endoscope information acquisition unit 331 acquires the identification information including the ID for identification of the ultrasound endoscope 2 input from the reception signal processing unit 32, and acquires various kinds of information such as the type and generation of the ultrasound endoscope 2 connected to the ultrasound observation apparatus 3.

The mode setting unit 332 acquires mode selection information received by a mode selection information input unit 381 of the input unit 38 to be described later, and sets an operation mode selected in the mode selection information from among a plurality of operation modes that may be executed by the ultrasound observation apparatus 3, as an operation mode to be actually executed. In the first embodiment, the case where the operation mode is at least one of the flow-mode, the elasto-mode, and the contrast medium-mode will be described as an example.

The flow-mode is a mode where a Doppler shift in a set region of interest is analyzed to detect blood, and two-dimensional information in which the presence or absence of blood flow and the direction of blood flow are color-coded is superimposed on a B-mode image. A B-mode image is a grayscale image in which the amplitude of reflected ultrasound waves is converted into luminance and presented in two-dimensions, based on RF data. The elasto-mode is a mode where, based on a difference (the amount of change) between a signal obtained when the ultrasound endoscope 2 is pressed against an observation target and a signal obtained when the ultrasound endoscope 2 is not pressed against the observation target, information on the hardness of the observation target in a region of interest is acquired, and color information corresponding to the hardness is superimposed on a B-mode image. The contrast medium-mode is a mode where an ultrasound contrast medium is used in combination to image harmonic components from the ultrasound contrast medium. In this mode, when the ultrasound contrast medium is injected into blood, blood flow information in a region of interest set broadly is acquired, and color information corresponding to the blood flow information is superimposed on a B-mode image.

The region-of-interest setting method selection unit 333 selects, from among a plurality of different region-of-interest setting methods previously associated with different operation modes, a region-of-interest setting method associated with an operation mode selected in mode selection information, that is, an operation mode set as an operation mode to be actually executed. The region-of-interest setting method selection unit 333 selects a region-of-interest setting method in consideration of the identification information on the ultrasound endoscope 2 in addition to the operation mode. The region-of-interest setting method selection unit 333 selects, from among a plurality of different region-of-interest setting methods previously associated with different combinations of operation modes and pieces of identification information on the ultrasound endoscope 2, a region-of-interest setting method associated with an operation mode selected in mode selection information and the identification information on the ultrasound endoscope 2 acquired by the endoscope information acquisition unit 331. The plurality of different region-of-interest setting methods is stored in a region-of-interest setting method table 391 of the storage unit 39 to be described later, in association with the different operation modes.

The region-of-interest setting unit 334 sets a region of interest suitable for an operation mode set as an operation mode to be actually executed by calculation using a region-of-interest setting method selected by the region-of interest setting method selection unit 333, based on a desired region selected in region selection information received by a region selection information input unit 382 of the input unit 38 to be described later.

The image processing unit 34 generates various images for digital display based on RF data received from the reception signal processing unit 32. The image processing unit 34 is implemented using a CPU, various arithmetic circuits, or the like. The image processing unit 34 includes an image generation unit 35 and an image composition unit 36.

The image generation unit 35 generates various images by performing coordinate conversion processing, interpolation processing, image filtering processing, correlation processing, and the like. The image generation unit 35 includes a B-mode image generation unit 351, a flow-mode image generation unit 352, an elasto-mode image generation unit 353, a contrast medium-mode image generation unit 354, and a boundary image generation unit 355.

The B-mode image generation unit 351 generates a B-mode image that is an ultrasound image (observation image) displayed by converting the amplitude of RF data into luminance. A B-mode image is a grayscale image in which the values of R (red), G (green), and B (blue) that are variables when the RGB color system is adopted as a color space are equated. The B-mode image generation unit 351 outputs, to the image composition unit 36, a B-mode image generated by sequentially performing image processing on digital RF data output from the reception signal processing unit 32.

The flow-mode image generation unit 352, the elasto-mode image generation unit 353, and the contrast medium-mode image generation unit 354 generate an operation mode image in which additional information obtained by performing processing such as an operation suitable for the operation mode on a region of interest set by the region-of-interest setting unit 334 is presented in two dimensions.

The flow-mode image generation unit 352 generates an operation mode image suitable for the flow-mode. The flow-mode image generation unit 352 analyzes a Doppler shift in a region of interest to acquire blood flow information on the position of a blood vessel and the flow of blood as additional information, and generates a flow-mode image that shows two-dimensional information in which the presence or absence of a blood vessel and the direction of blood flow are color-coded.

The elasto-mode image generation unit 353 generates an operation mode image suitable for the elasto-mode. The elasto-mode image generation unit 353 acquires information on the hardness of an observation target in a region of interest as additional information, based on a difference (the amount of change) between a signal obtained when the ultrasound endoscope 2 is pressed against the observation target and a signal obtained when the ultrasound endoscope 2 is not pressed against the observation target, and generates an elasto-mode image showing color information corresponding to the hardness in two dimensions.

The contrast medium-mode image generation unit 354 generates an operation mode image suitable for the contrast medium-mode. The contrast medium-mode image generation unit 354 acquires blood flow information based on harmonic components from the ultrasound contrast medium as additional information, and generates a contrast medium-mode image showing color information corresponding to the blood flow information in two dimensions.

The boundary image generation unit 355 generates a boundary image showing mesh-like boundaries that divide a B-mode image into a plurality of divided regions at the time of superimposition on the B-mode image. The boundary image generation unit 355 generates a boundary image showing boundaries for dividing a B-mode image displayed on the display device 4 into a plurality of regions. A predetermined pattern is set as a default boundary pattern showing the positions or shapes of boundaries or the number of boundary lines delimiting regions. The operator may enter instruction information instructing the change of the positions or shapes of boundaries or the number of boundary lines from the input unit 38, thereby changing the boundary pattern, changing the number, sizes, shapes, etc. of divided regions. The boundary image generation unit 355 generates a boundary image showing region identification information for identifying regions of a B-mode image in positions corresponding to the regions, together with boundaries.

The image composition unit 36 includes a boundary image composition unit 361 for generating a boundary composite image into which a B-mode image generated by the B-mode image generation unit 351 and a boundary image generated by the boundary image generation unit 355 are composited such that the boundary image is superimposed on the B-mode image, and a mode image composition unit 362 for generating a mode composite image in which an operation mode image generated by the flow-mode image generation unit 352, the elasto-mode image generation unit 353, or the contrast medium-mode image generation unit 354 is superimposed on a B-mode image generated by the B-mode image generation unit 351. The boundary image composition unit 361 generates a boundary composite image obtained by processing an ultrasound image displayed on the display device 4 such that a plurality of divided regions divided by mesh-like boundaries is displayed on the ultrasound image. The image composition unit 36 holds an input B-mode image in a buffer not illustrated, extracts a B-mode image to be composited from the buffer at the time of generating a composite image, and generates a composite image in which an operation mode image or a boundary image is superimposed on the extracted B-mode image. The image composition unit 36 also performs processing of superimposing a character image or a small screen image on a B-mode image.

The display control unit 37 performs predetermined processing such as a reduction of data according to a data step width that depends on an image display range on the display device 4 and gradation processing on a B-mode image generated by the B-mode image generation unit 351 or a composite image generated by the image composition unit 36, and then outputs the processed image to the display device 4 as an image for display. As a result, a boundary composite image in which boundaries and region identification information are presented on a B-mode image is displayed on the display device 4. Or a mode composite image in which additional information suitable for each operation mode is superimposed in two dimensions on a B-mode image is displayed on the display device 4.

The input unit 38 is implemented by an input device for receiving input of various kinds of information. The input unit 38 includes a mode selection information input unit 381 for receiving input of mode selection information selecting a desired operation mode from a plurality of settable operation modes, and a region selection information input unit 382 for receiving input of region selection information selecting a desired region from a plurality of regions in a B-mode image divided by boundaries in a boundary image. The region selection information input unit 382 receives region selection information input by voice. The region selection information input unit 382 may be formed by a pointing device such as a track ball, and configured to receive region selection information input by a means other than voice. The mode selection information input unit 381 is formed by a pointing device, or may be configured to receive mode selection information input by voice. Mode selection information is information selecting either a first operation mode for detecting a selected one of a plurality of pieces of characteristic biological information or a second operation mode for detecting biological information different from characteristic biological information obtained in the first operation mode.

The storage unit 39 stores various programs for operating the ultrasound observation system 1, and data including various parameters necessary for the operation of the ultrasound observation system 1. The storage unit 39 stores various programs including an operation program for executing an operation method of the ultrasound observation system 1. The storage unit 39 is implemented using a ROM in which various programs and the like are preinstalled and a RAM storing calculation parameters, data, and the like for processing steps, for example. The storage unit 39 stores the region-of-interest setting method table 391 showing a plurality of different region-of-interest setting methods previously associated with different operation modes.

Figure 2:
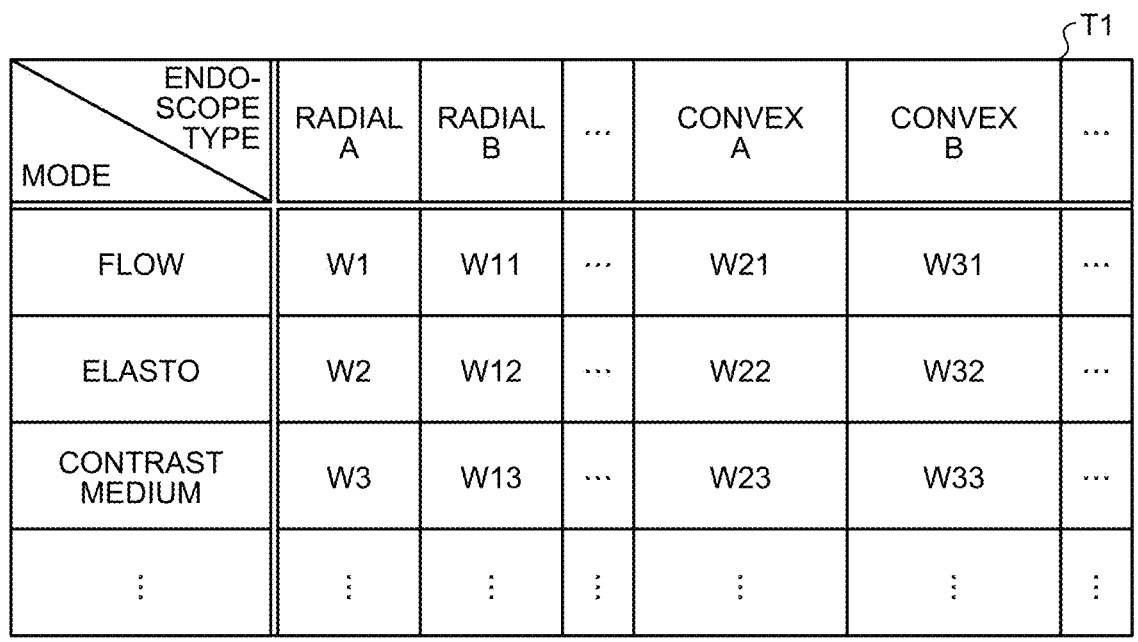
FIG. 2 is a diagram illustrating an example of a region-of-interest setting method table illustrated in FIG. 1.

FIG. 2 is a diagram illustrating an example of the region-of-interest setting method table 391. In the region-of-interest setting method table 391, as in a table T1 exemplified in FIG. 2, a plurality of region-of-interest setting method numbers W1 to W33 for identifying different region-of-interest setting methods are previously associated with different combinations of operation modes and pieces of type information on the ultrasound endoscope 2. The region-of-interest setting method numbers W1 to W33 are associated with execution programs for the different region-of-interest setting methods corresponding to the numbers. The region-of-interest setting method selection unit 333 refers to the table T1 and selects a region-of-interest setting method number associated with an operation mode selected in mode selection information and the type of the ultrasound endoscope 2. The region-of-interest setting unit 334 sets a region of interest suitable for an operation mode, using an execution program for a region-of-interest setting method corresponding to a region-of-interest setting method number selected by the region-of-interest setting method selection unit 333.

Figure 3:
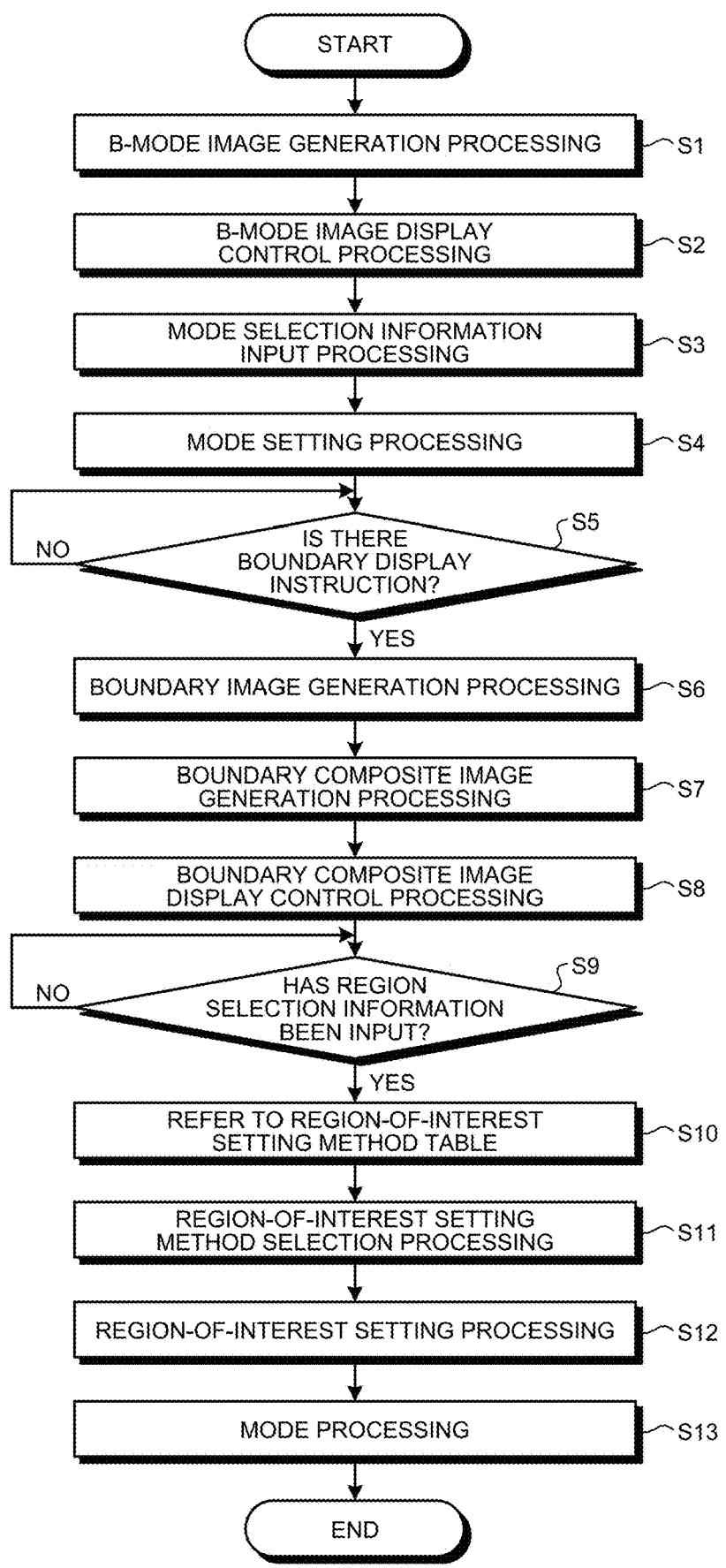
FIG. 3 is a flowchart illustrating a processing procedure for an ultrasound observation apparatus illustrated in FIG. 1 to set a region of interest and generate a composite image for the set region of interest.

Next, an operation method of the ultrasound observation apparatus 3 illustrated in FIG. 1 will be described. FIG. 3 is a flowchart illustrating a processing procedure for the ultrasound observation apparatus 3 to set a region of interest and generate a composite image for the set region of interest.

Figure 4:
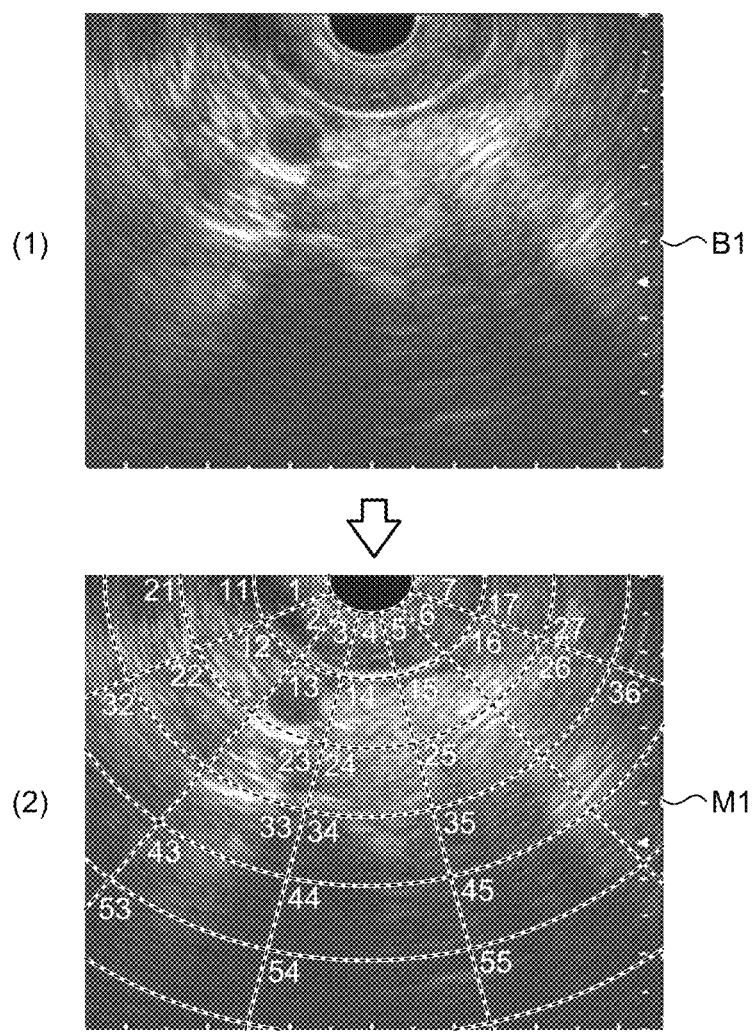
FIG. 4 is a diagram illustrating an example of a B-mode image generated by the ultrasound observation apparatus illustrated in FIG. 1 and a boundary composite image obtained by superimposing a boundary image on the B-mode image.

As illustrated in FIG. 3, in the ultrasound observation apparatus 3, the B-mode image generation unit 351 performs B-mode image generation processing to generate a B-mode image by processing RF data generated by the reception signal processing unit 32 based on an echo signal generated by the ultrasound transducer 21 after the transmission unit 31 transmits a pulse signal for the B-mode image to the ultrasound transducer 21 (step S1). The display control unit 37 performs B-mode image display control processing to output the B-mode image to the display device 4 and cause the display device 4 to display it (step S2). FIG. 4 is a diagram illustrating an example of a B-mode image generated by the ultrasound observation apparatus 3 and a boundary composite image obtained by superimposing a boundary image on the B-mode image. A B-mode image is a grayscale image in which the amplitude of RF data is converted into luminance and presented in two dimensions like a B-mode image B1 in (1) of FIG. 4. The endoscope information acquisition unit 331 has acquired the identification information on the ultrasound endoscope 2 from the endoscope information memory 22 at the time of connection of the ultrasound endoscope 2 to the ultrasound observation apparatus 3. The control unit 33 has already stored information such as the type and generation of the ultrasound endoscope 2 connected to the ultrasound observation apparatus 3 at a stage in step S1.

The mode selection information input unit 381 performs mode selection information input processing to receive input of mode selection information selecting a desired operation mode from a plurality of operation modes (step S3). The mode selection information is input from the mode selection information input unit 381 to the control unit 33 by the input device being operated by the operator, or input by voice.

The mode setting unit 332 performs mode setting processing to acquire mode selection information received by the mode selection information input unit 381 and set the operation mode selected in the mode selection information from among the plurality of operation modes which may be executed by the ultrasound observation apparatus 3 as an operation mode to be actually executed (step S4). For a region of interest, a predetermined region is set as default. By the processing operations of the units of the ultrasound observation apparatus 3, an operation mode image for the region of interest set as default is generated and displayed on the display device 4, superimposed on a B-mode image.

The control unit 33 determines whether there is a boundary display instruction (step S5). The control unit 33 determines whether there is a boundary display instruction, based on the presence or absence of input of instruction information instructing superimposed display of a boundary image on the B-mode image. The instruction information is input from the input unit 38 to the control unit 33 by the input device being operated by the operator, or input by voice. For example, when the operator utters "boundary", instruction information instructing superimposed display of a boundary image on the B-mode image is input to the control unit 33. When the control unit 33 determines that this boundary display instruction is not provided (step S5: No), the control unit 33 repeats the determination processing in step S5 until instruction information is input.

When the control unit 33 determines that there is a boundary display instruction (step S5: Yes), the boundary image generation unit 355 performs boundary image generation processing to generate a boundary image showing boundaries that divide the B-mode image into a plurality of regions (step S6). The boundary image composition unit 361 performs boundary composite image generation processing to generate a boundary composite image in which the boundary image generated in step S6 is superimposed on the B-mode image to be composited (step S7). The display control unit 37 performs boundary composite image display control processing to cause the display device 4 to display the boundary composite image (step S8). In step S8, as exemplified in (2) of FIG. 4, a boundary composite image M1 is displayed in which a boundary image with a plurality of boundaries positioned in a predetermined pattern set as default is superimposed on the B-mode image B1. As illustrated in the boundary composite image M1, in the boundary composite image, region numbers (region identification information) for identifying regions of the B-mode image B1 are illustrated in positions corresponding to the regions, together with broken lines indicating the boundaries.

The control unit 33 determines whether region selection information has been input (step S9). The control unit 33 determines whether region selection information has been input, based on whether region selection information input processing to receive input of region selection information has been performed in the region selection information input unit 382. Region selection information is input by voice. Alternatively, region selection information may be input to the region selection information input unit 382 by the operation of the input device by the operator. When the control unit 33 determines that there is no input of this region selection information (step S9: No), the control unit 33 repeats the determination processing in step S9 until region selection information is input.

When the control unit 33 determines that region selection information has been input (step S9: Yes), that is, when the region selection information input unit 382 has performed the region selection information input processing to receive input of region selection information, the region-of-interest setting method selection unit 333 refers to the region-of-interest setting method table 391 stored in the storage unit 39 (step S10). The region-of-interest setting method selection unit 333 performs region-of-interest setting method selection processing to select a region-of-interest setting method associated with the operation mode set in the mode setting processing from among a plurality of region-of-interest setting methods in the region-of-interest setting method table 391 referred to (step S11). As exemplified in the table T1 in FIG. 2, in the region-of-interest setting method table 391, different region-of-interest setting methods are associated with different combinations of operation modes and pieces of type information on the ultrasound endoscope 2. The region-of-interest setting method selection unit 333 selects a region-of-interest setting method associated with the operation mode set in the mode setting processing and the type and generation of the ultrasound endoscope 2 connected to the ultrasound observation apparatus 3, from among the plurality of region-of-interest setting methods in the region-of-interest setting method table 391 referred to.

The region-of-interest setting unit 334 performs region-of-interest setting processing to set again a region of interest suitable for the operation mode and the endoscope type and the like of the ultrasound endoscope 2 on the B-mode image by calculation using the region-of-interest setting method selected in the region-of-interest setting method selection processing, based on the desired region selected in the region selection information (step S12).

The ultrasound observation apparatus 3 performs mode processing in which the image processing unit 34 generates an operation mode image presented in two dimensions additional information obtained by performing processing suitable for the operation mode set in the mode setting processing on the region of interest set again by the region-of-interest setting processing, the image composition unit 36 generates a mode composite image in which the operation mode image is superimposed on the B-mode image to be composited, and the display control unit 37 causes the display device 4 to display the mode composite image (step S13). FIG. 3 is an example of the processing procedure of the ultrasound observation apparatus 3. There may be cases where region information is input before mode selection information is input.

Next, the region-of-interest setting method selection processing and the region-of-interest setting processing illustrated in FIG. 3 will be described. When the endoscope type of the ultrasound endoscope 2 connected to the ultrasound observation apparatus 3 is a radial A type, and the flow-mode is selected as the operation mode, the region-of-interest setting method selection unit 333 selects the region-of-interest setting method corresponding to the region-of-interest setting method number W1 from among the plurality of region-of-interest setting method numbers W1 to W33 presented in the table T1 in FIG. 2. When a first region and a second region are selected in the region selection information, the region-of-interest setting method corresponding to the region-of-interest setting method number W1 is a method to set, as a region of interest, the first region and the second region, and a region through which, among acoustic rays passing through the first region and the second region, acoustic rays of depths between the shallowest depth and the deepest depth pass. For example, ultrasound signals on the same boundary among the curved boundaries along the scanning direction of the ultrasound transducer in the boundary composite image M1 may be said to have an equal ultrasound signal reception depth. FIGS. 5 to 8 are diagrams for explaining the region-of-interest setting method corresponding to the region-of-interest setting method number W1.

Figure 5:
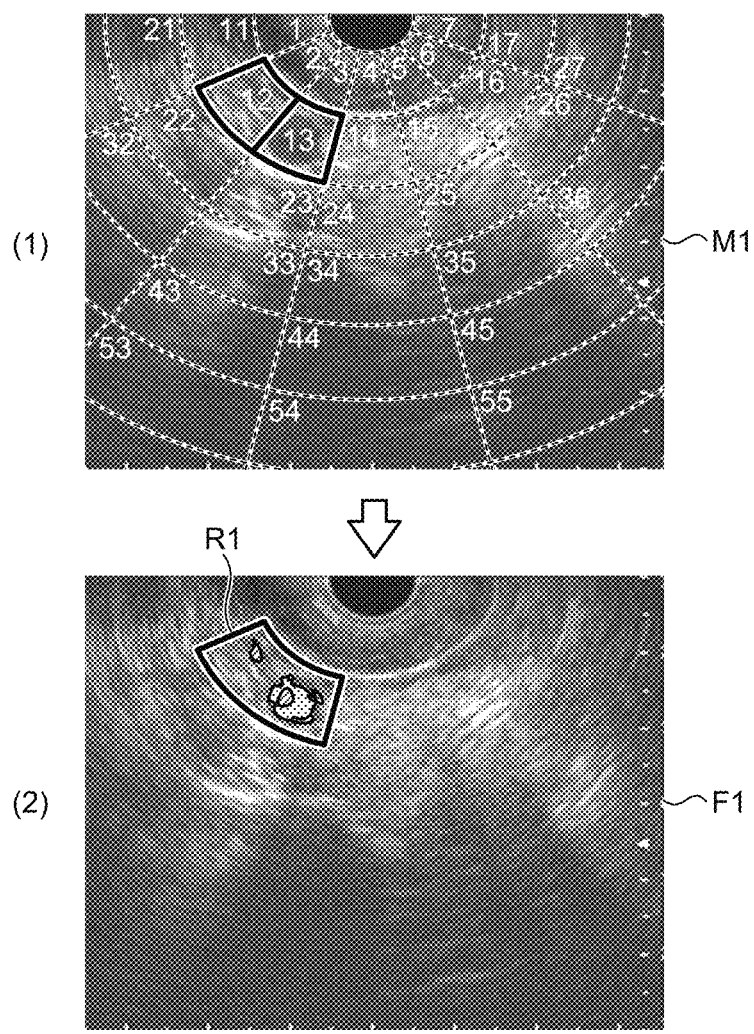
FIG. 5 is a diagram for explaining an example of a region-of-interest setting method.

For example, when the operator utters "12, 13", the region selection information input unit 382 receives the input of a region selection signal selecting a region 12 and a region 13 of the boundary composite image M1 (see (1) of FIG. 5). As illustrated in the boundary composite image M1 in (1) of FIG. 5, since the selected regions 12 and 13 are adjacent to each other, the region-of-interest setting unit 334 uses the region-of-interest setting method corresponding to the region-of-interest setting method number W1, thereby setting a region R1 into which the region 12 and the region 13 are combined as a region of interest (see (2) of FIG. 5). As a result, the flow-mode image generation unit 352 generates a flow-mode image in which the presence or absence of blood flow and the direction of blood flow in the region R1 are color-coded. The display device 4 thus displays a mode composite image F1 in which color information corresponding to the direction of blood flow is superimposed on the region R1 on the B-mode image B1 (see (2) of FIG. 5).

Figure 6:
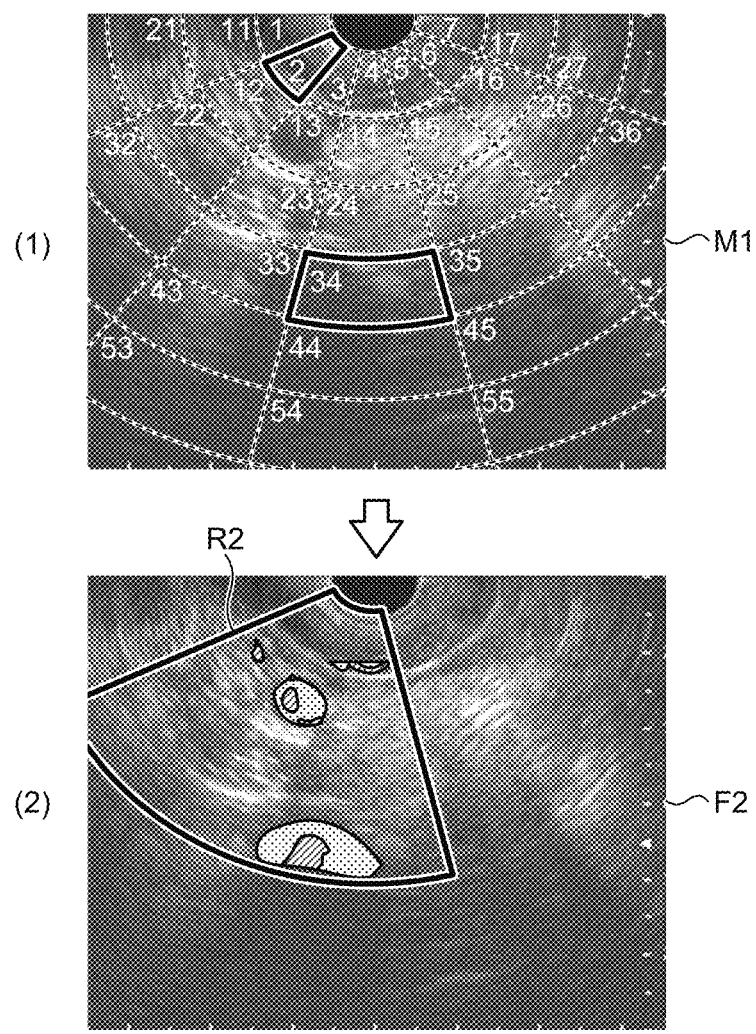
FIG. 6 is a diagram for explaining an example of the region-of-interest setting method.

When the operator utters "2, 34", the region selection information input unit 382 receives the input of a region selection signal selecting a region 2 and a region 34 of the boundary composite image M1 (see (1) of FIG. 6). As illustrated in a boundary composite image M1 in (1) of FIG. 6, when the region 2 and the region 34 are selected, the region-of-interest setting unit 334 uses the region-of-interest setting method corresponding to the region-of-interest setting method number W1, thereby setting, as a region of interest, a region R2 containing the region 2 and the region 34, and regions 3, 4, 12 to 14, 22 to 24, 32, and 33 through which, among acoustic rays passing through the region 2 and the region 34, acoustic rays of depths between the shallowest depth and the deepest depth pass (see (2) of FIG. 6). As a result, the flow-mode image generation unit 352 generates a flow-mode image in which the presence or absence of blood flow and the direction of blood flow are color-coded for the region R2. The display device 4 thus displays a mode composite image F2 in which two-dimensional information color-coded in the presence or absence of blood flow and the direction of blood flow is superimposed on the region R2 on the B-mode image B1 (see (2) of FIG. 6). According to the region-of-interest setting method corresponding to the region-of-interest setting method number W1, in order for the operator to set, as a region of interest, a region where the operator wants to visually check blood flow information, the operator only needs to utter a region number representing a starting point and a region number representing an end point of the region to be visually checked.

Figure 7:
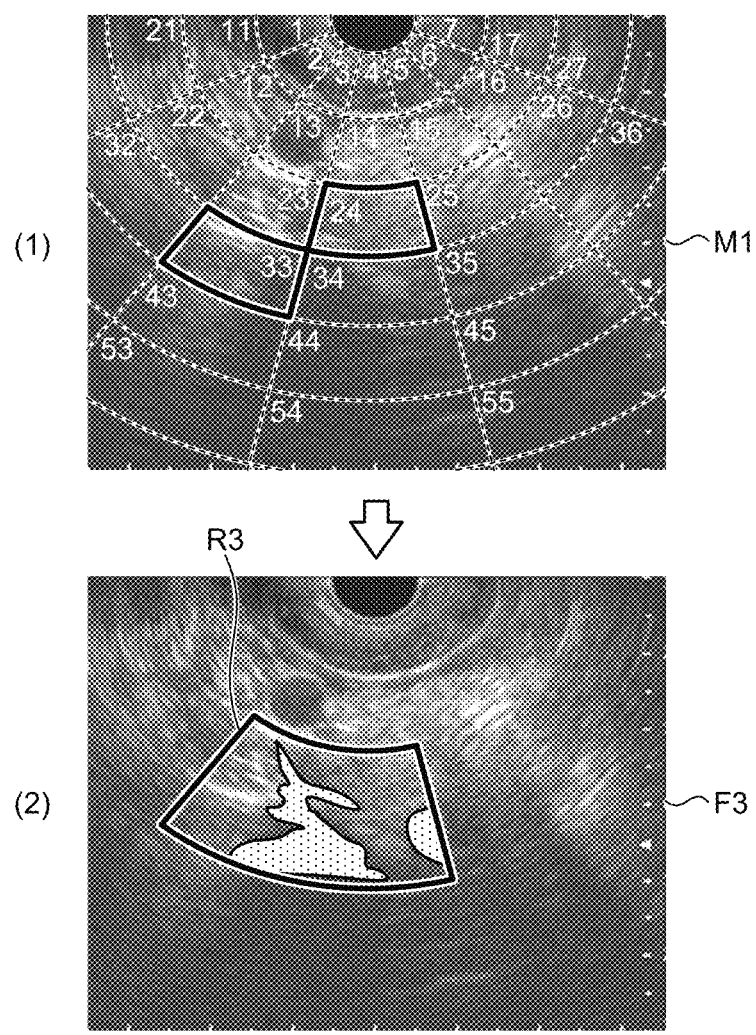
FIG. 7 is a diagram for explaining an example of the region-of-interest setting method.
Figure 8:
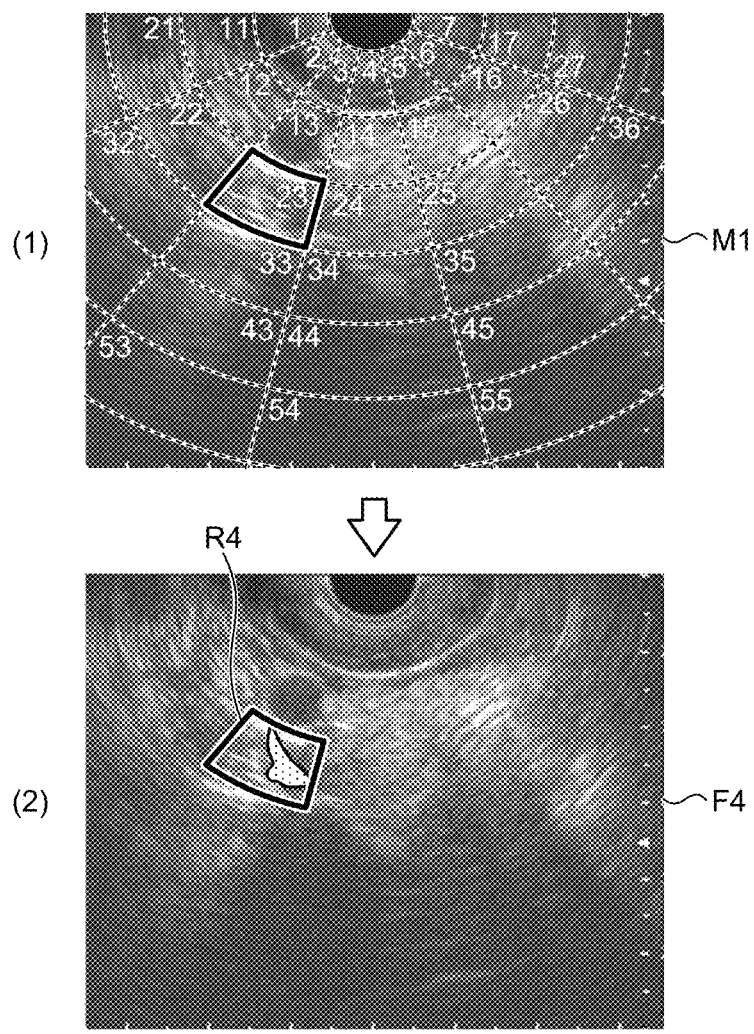
FIG. 8 is a diagram for explaining an example of the region-of-interest setting method.

When the operator utters "24, 33", the region selection information input unit 382 receives the input of a region selection signal selecting a region 24 and a region 33 of the boundary composite image M1 (see (1) of FIG. 7). In this case, the region-of-interest setting unit 334 uses the region-of-interest setting method corresponding to the region-of-interest setting method number W1, thereby setting, as a region of interest, a region R3 containing the region 24 and the region 33, and regions 23 and 34 through which, among acoustic rays passing through the region 24 and the region 33, acoustic rays of depths between the shallowest depth and the deepest depth pass (see (2) of FIG. 7). As a result, the flow-mode image generation unit 352 generates a flow-mode image in the region R3. The display device 4 thus displays a mode composite image F3 in which two-dimensional information color-coded in the presence or absence of blood flow and the direction of blood flow is superimposed on the region R3 on the B-mode image B1 (see (2) of FIG. 7). When the operator utters "23", that is, when a single region is selected in region selection information (see (1) of FIG. 8), as illustrated in (2) of FIG. 8, the region-of-interest setting unit 334 uses the region-of-interest setting method corresponding to the region-of-interest setting method number W1, thereby setting the region 23 (region R4) as a region of interest. The display device 4 thus displays a mode composite image F4 in which two-dimensional information color-coded in the presence or absence of blood flow and the direction of blood flow is superimposed on the region R4 on the B-mode image B1 (see (2) of FIG. 8).

When the endoscope type of the ultrasound endoscope 2 connected to the ultrasound observation apparatus 3 is the radial A type, and the elasto-mode is selected as the operation mode, the region-of-interest setting method selection unit 333 selects the region-of-interest setting method corresponding to the region-of-interest setting method number W2 from among the plurality of region-of-interest setting method numbers W1 to W33 presented in the table T1 in FIG. 2. When a first region and a second region are selected in region selection information, the region-of-interest setting method corresponding to the region-of-interest setting method number W2 is a method to set, as a region of interest, a region with its vertices at the midpoints of diagonal lines of the first region and the second region, and of regions through which, among acoustic rays passing through the first region and the second region, acoustic rays of depths between the shallowest depth and the deepest depth pass, in the regions.

Figure 9:
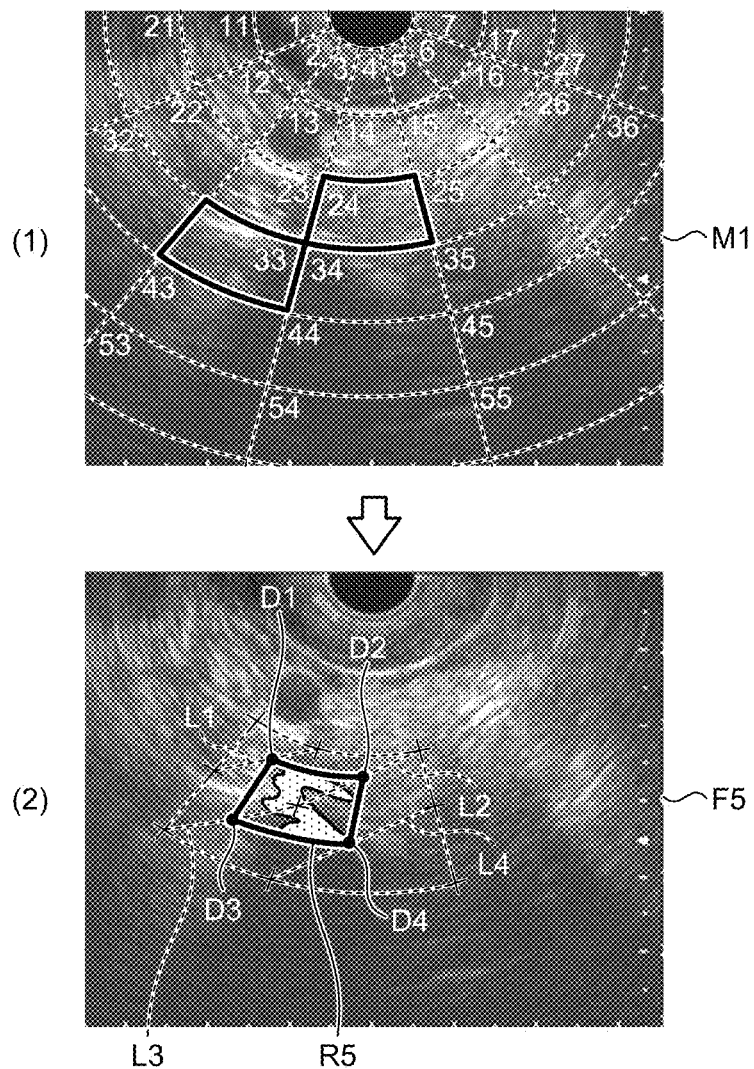
FIG. 9 is a diagram for explaining an example of a region-of-interest setting method.

FIG. 9 is a diagram for explaining the region-of-interest setting method corresponding to the region-of-interest setting method number W2. For example, when the operator utters "24, 33", the region selection information input unit 382 receives the input of a region selection signal selecting the region 24 and the region 33 of the boundary composite image M1 (see (1) of FIG. 9). In this case, the region-of-interest setting unit 334 uses the region-of-interest setting method corresponding to the region-of-interest setting method number W2, thereby, as illustrated in (2) of FIG. 9, setting, as a region of interest, a region R5 with its vertices at the midpoints D1 to D4 of diagonal lines L1 to L4 of the region 24 and the region 33, and of the regions 23 and 34 through which, among acoustic rays passing through the region 24 and the region 33, acoustic rays of depths between the shallowest depth and the deepest depth pass, in the regions. As a result, the elasto-mode image generation unit 353 generates an elasto-mode image showing color information corresponding to the hardness of the observation target in the region R5. The display device 4 thus displays a mode composite image F5 in which the color information corresponding to the hardness is superimposed on the region R5 on the B-mode image B1 (see (2) of FIG. 9).

Since the elasto-mode is a mode for showing the relative hardness of tissue in a region of interest, even when an object of diagnosis is contained within a region of interest, the color of the object changes depending on the position and size of the region of interest. Thus, it is necessary to optimize the position and size of a region of interest suitably for an object of diagnosis. Here, if an object of diagnosis is present between the region 24 and the region 33, and a region of interest is set so as to contain the regions 23, 24, 33, and 34, using the region-of-interest setting method number W1, a region occupied by the object of diagnosis is relatively smaller than a region occupied by other objects, so that the hardness of the object of diagnosis is not precisely displayed. By contrast, the region-of-interest setting method corresponding to the region-of-interest setting method number W2 is a method to set, as a region of interest, the region R5 enclosed with its vertices at the midpoints D1 to D4 of the diagonal lines L1 to L4 of the regions 23, 24, 33, and 34, in the regions. That is, even when the regions 24 and 33 in which the object of diagnosis is present are selected directly, a region of interest is automatically set so that the region occupied by the object of diagnosis forms a proper proportion. Consequently, according to this region-of-interest setting method, a region suitable for the elasto-mode is set as a region of interest, so that measurement accuracy (display accuracy) in the elasto-mode may be increased.

When the endoscope type of the ultrasound endoscope 2 connected to the ultrasound observation apparatus 3 is the radial A type, and the contrast medium-mode is selected as the operation mode, the region-of-interest setting method selection unit 333 selects the region of interest setting method corresponding to the region-of-interest setting method number W3 from among the plurality of region-of-interest setting method numbers W1 to W33 presented in the table T1 in FIG. 2. The region-of-interest setting method corresponding to the region-of-interest setting method number W3 is a method to set, as a region of interest, a region selected in region selection information and a region in a predetermined range around the region.

Figure 10:
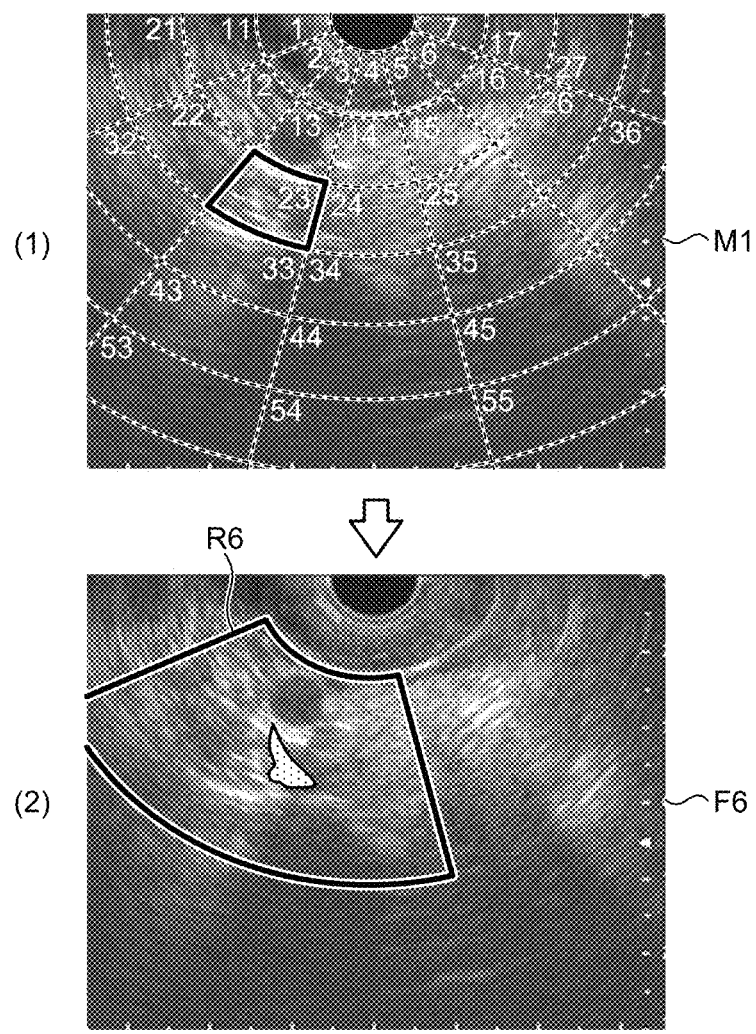
FIG. 10 is a diagram for explaining an example of a region-of-interest setting method.

FIG. 10 is a diagram for explaining the region-of-interest setting method corresponding to the region-of-interest setting method number W3. For example, when the operator utters "23", the region selection information input unit 382 receives the input of a region selection signal selecting the region 23 of the boundary composite image M1 (see (1) of FIG. 10). In this case, as illustrated in (2) of FIG. 10, the region-of-interest setting unit 334 sets, as a region of interest, a region R6 containing the region 23 selected in the region selection information and all the regions 12 to 14, 22, 24, and 32 to 34 adjoining the region 23. As a result, the contrast medium-mode image generation unit 354 generates a contrast medium-mode image showing color information corresponding to blood flow information based on harmonic components from the ultrasound contrast medium in the region R6. The display device 4 thus displays a mode composite image F6 in which the color information corresponding to the blood flow information is superimposed on the region R6 on the B-mode image B1 (see (2) of FIG. 10). In the contrast medium-mode, it is generally necessary to visually check a relatively wide region. According to the region-of-interest setting method corresponding to the region-of-interest setting method number W3, the operator may set a wide region to be visually checked actually as a region of interest only by uttering only a region in the vicinity of the center of the region to be checked.

When the endoscope type of the ultrasound endoscope 2 connected to the ultrasound observation apparatus 3 is a convex A type, and the flow-mode is selected as the operation mode, the region-of-interest setting method selection unit 333 selects the region-of-interest setting method corresponding to the region-of-interest setting method number W21 from among the plurality of region-of-interest setting method numbers W1 to W33 presented in the table T1 in FIG. 2. The region-of-interest setting method corresponding to the region-of-interest setting method number W21 is a method to set a region of interest such that at least a region selected in region selection information and a region containing a path along which the tip of the puncture needle passes are contained.

Figure 11:
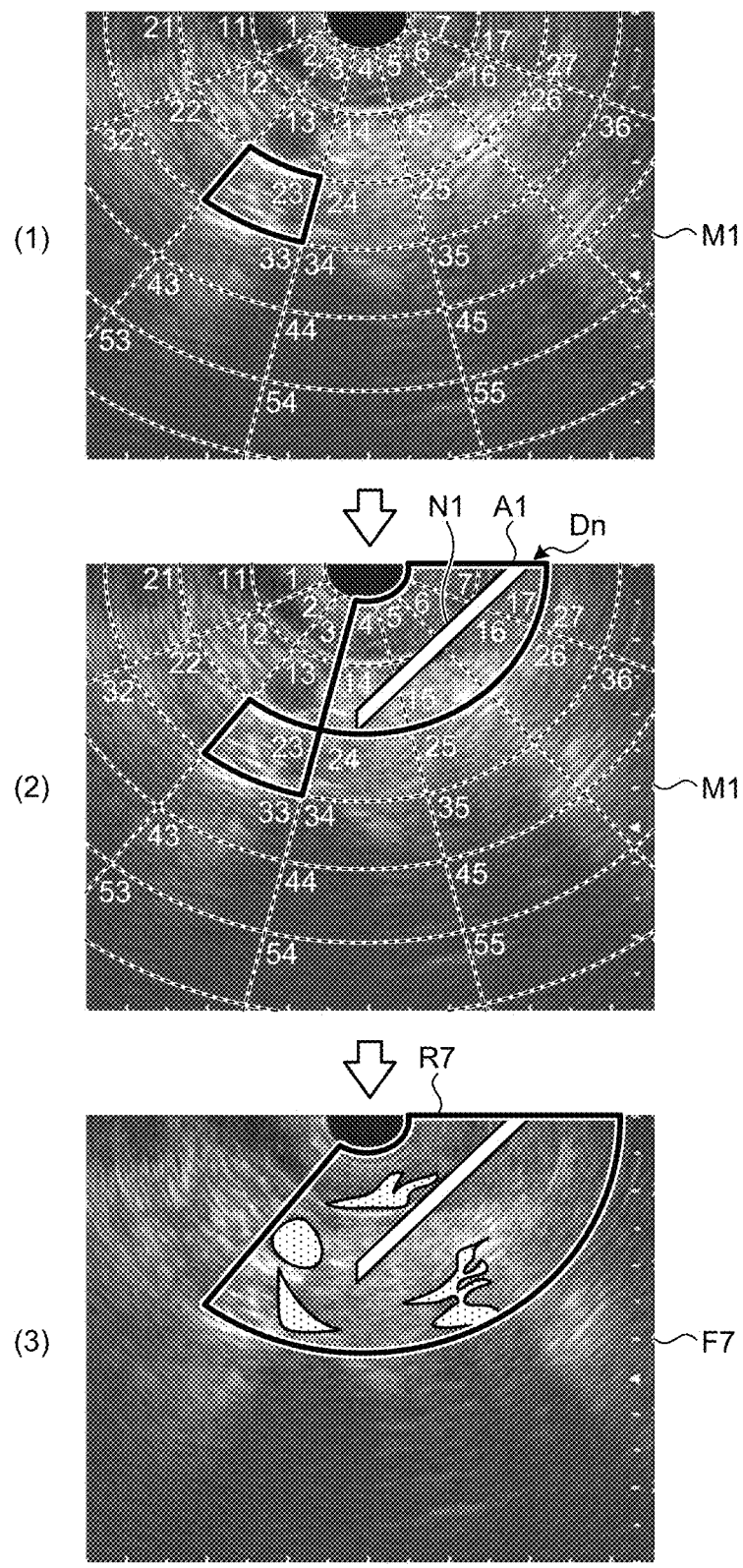
FIG. 11 is a diagram for explaining an example of a region-of-interest setting method.
Figure 12:
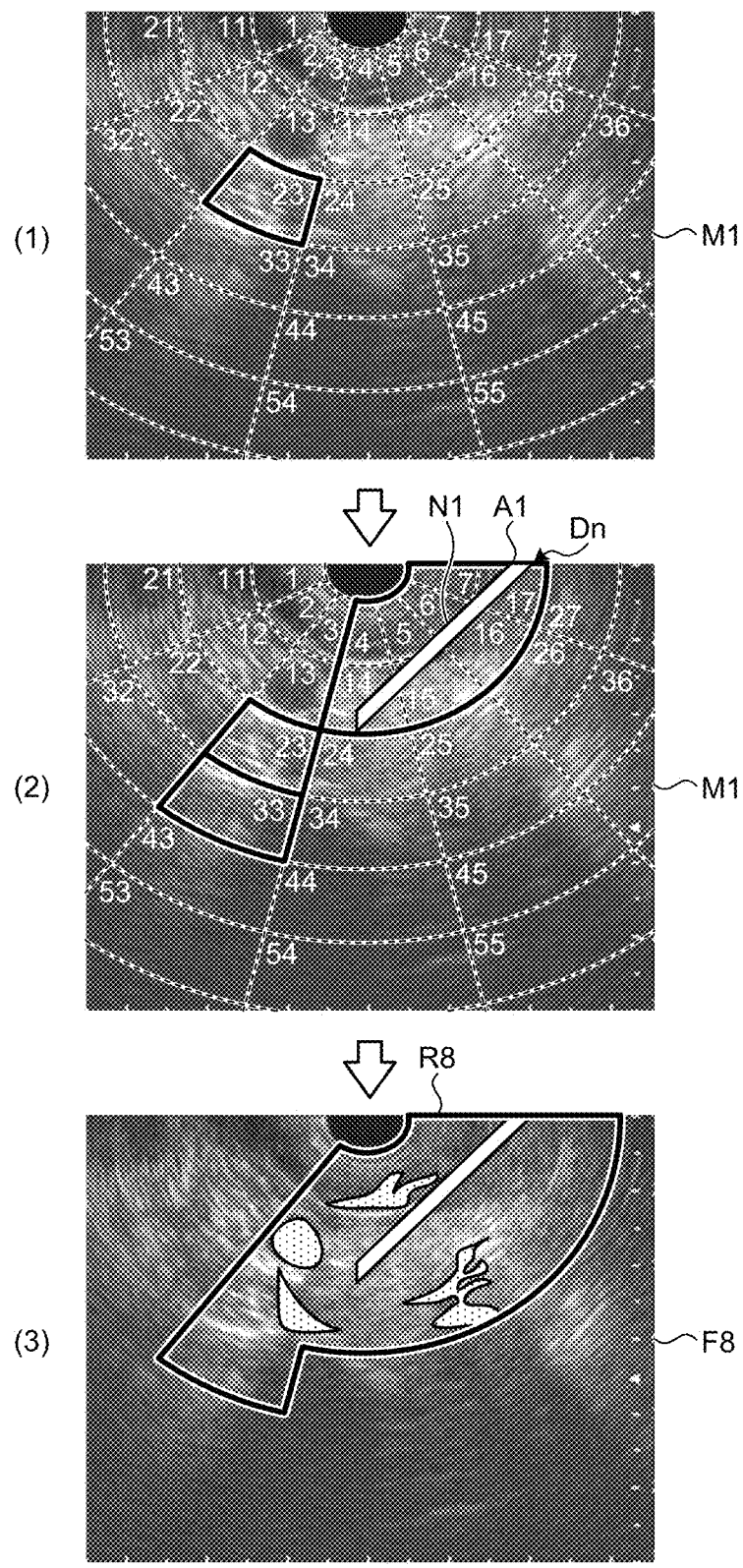
FIG. 12 is a diagram for explaining an example of the region-of-interest setting method.

FIGS. 11 and 12 are diagrams for explaining the region-of-interest setting method corresponding to the region-of-interest setting method number W21. In FIGS. 11 and 12, a position Dn corresponds to the distal end opening through which the puncture needle protrudes from the ultrasound endoscope 2. For example, when the operator utters "23", the region selection information input unit 382 receives the input of a region selection signal selecting the region 23 of the boundary composite image M1 (see (1) of FIG. 11). In this case, as illustrated in (2) of FIG. 11, the region-of-interest setting unit 334 sets, as a region of interest, a region containing the region 23 selected in the region selection information and a region A1 containing a path N1 along which the tip of the puncture needle passes (regions 4 to 7 and 14 to 17), specifically, a wide region R7 containing regions 3 to 7, 13 to 17, and 23 to 27 from the region 23 to the region A1 (see (3) of FIG. 11). As a result, the flow-mode image generation unit 352 generates a flow-mode image showing color information corresponding to the direction of blood flow in the region R7. The display device 4 thus displays a mode composite image F7 in which two-dimensional information color-coded in the presence or absence of blood flow and the direction of blood flow is superimposed on the region R7 on the B-mode image B1 (see (3) of FIG. 11). As described above, when the endoscope type of the ultrasound endoscope 2 is the convex A type, processing suitable for the flow-mode is performed on the region R7 with the position Dn corresponding to the distal end opening through which the tip of the puncture needle protrudes as the starting point, and with the region 23 selected by the operator as the end point. Thus, by visually checking the mode composite image F7, the operator may see the thickness of a blood vessel and the like located on the path of the puncture needle and around the path, and may protrude the puncture needle along an optimal path.

The region-of-interest setting method corresponding to the region-of-interest setting method number W21 may set, as a region of interest, a region R8 containing also the region 33 that may be presumed to be reached by the tip of the puncture needle at the time of the maximum protrusion of the puncture needle (see (2) of FIG. 12), in addition to the region containing the regions 3 to 7, 13 to 17, and 23 to 27 from the region 23 selected in the region selection information (see (1) of FIG. 12) to the region A1 containing the path along which the tip of the puncture needle passes (see (2) of FIG. 12). Since the position Dn corresponding to the distal end opening through which the tip of the puncture needle protrudes, and the approximate protrusion direction of the puncture needle and the maximum protrusion length of the puncture needle are known, it is possible to estimate a region reached by the tip of the puncture needle at the time of the maximum protrusion of the puncture needle. The display device 4 displays a mode composite image F8 in which two-dimensional information color-coded in the presence or absence of blood flow and the direction of blood flow is superimposed on the region R8 on the B-mode image B1 (see (3) of FIG. 12). Thus, a region of interest may be set such that a flow-mode image is displayed also on the region R8 additionally containing the region 33 that may be presumed to be reached by the tip of the puncture needle at the time of the maximum protrusion of the puncture needle.

As described above, the first embodiment includes the region-of-interest setting unit 334 for resetting a region of interest by calculation using a region-of-interest setting method associated with an operation mode selected in mode selection information selected from among a plurality of different region-of-interest setting methods previously associated with different operation modes. Therefore, according to the first embodiment, the operator only selects a desired region once from among a plurality of regions presented in a composite image of a boundary image and a B-mode image to cause the ultrasound observation apparatus 3 to automatically optimize a region of interest based on the desired region for each operation mode. That is, according to the operation mode, a region of interest may be optimized to be in a position and a size other than those of the desired region selected by the operator. Therefore, according to the first embodiment, a region of interest suitable for each operation mode may be set with a simple operation. The first embodiment does not construct new arithmetic processing for setting a region of interest, but only selects a region-of-interest setting method associated with an operation mode from among a plurality of different region-of-interest setting methods previously associated with different operation modes, thus being able to set a region of interest in a short time.

In the first embodiment, the region selection information input unit 382 receives input of region selection information by voice. Thus, according to the first embodiment, the operator only utters the identification number of a desired region once to cause the ultrasound observation apparatus 3 to automatically set a region of interest suitable for each operation mode. The operator thus does not have to operate a pointing device, releasing the hand from the ultrasound endoscope 2 in order to input region selection information.

According to the first embodiment, a region-of-interest setting method suitable for not only an operation mode but also the endoscope type, generation, etc. of the ultrasound endoscope 2 connected to the ultrasound observation apparatus 3 is selected to set a region of interest. Thus, a region of interest may be optimized for each endoscope type of the ultrasound endoscope 2.

Second Embodiment

Figure 13:
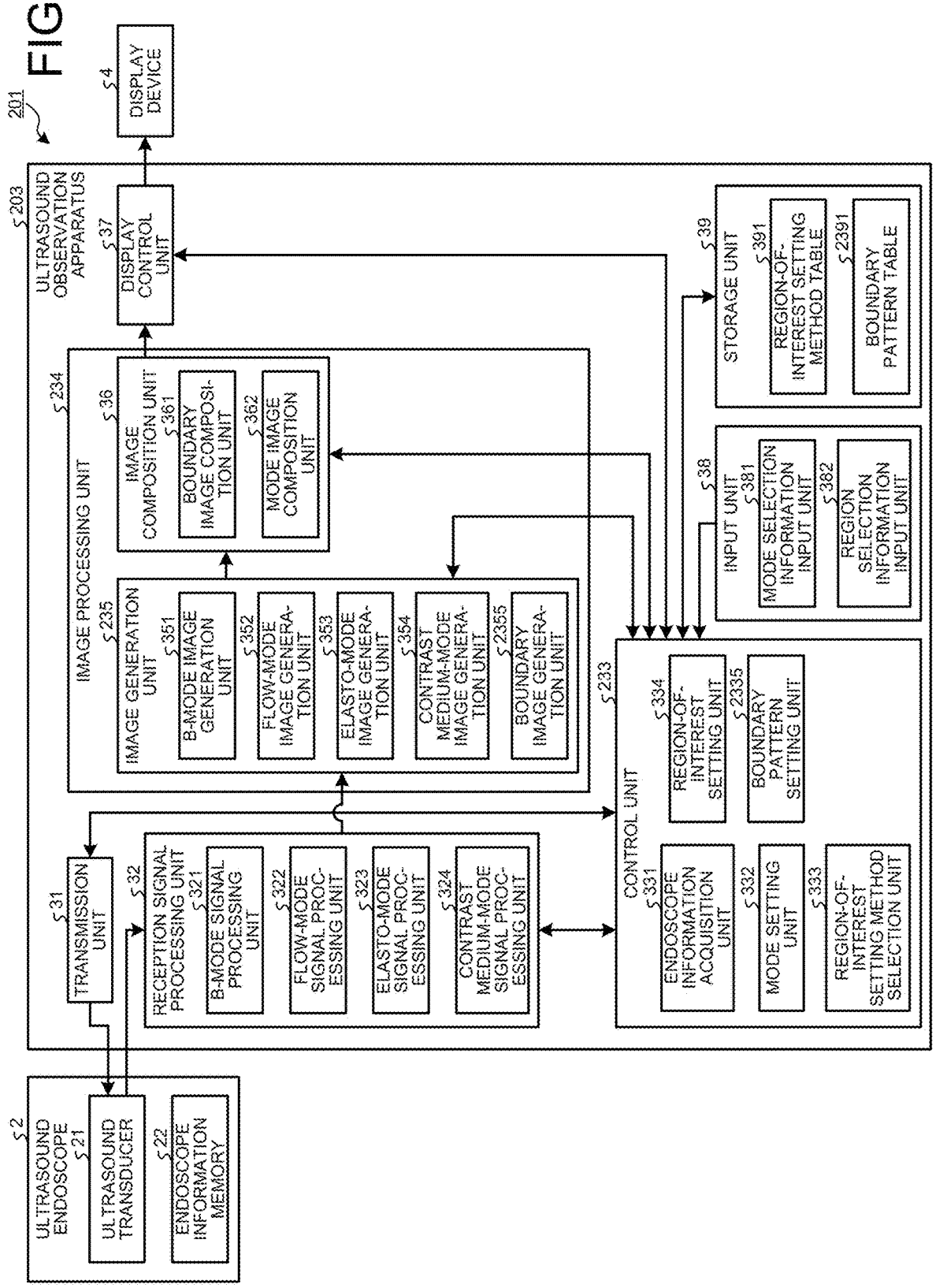
FIG. 13 is a block diagram illustrating a configuration of an ultrasound observation system according to a second embodiment.

Next, a second embodiment will be described. FIG. 13 is a block diagram illustrating a configuration of an ultrasound observation system according to the second embodiment. As illustrated in FIG. 13, an ultrasound observation system 201 according to the second embodiment includes an ultrasound observation apparatus 203 in place of the ultrasound observation apparatus 3 in FIG. 1. The ultrasound observation apparatus 203 includes a control unit 233 having a boundary pattern setting unit 2335, and an image processing unit 234 having an image generation unit 235. The image generation unit 235 has a boundary image generation unit 2355.

The boundary pattern setting unit 2335 selects a boundary pattern suitable for an operation mode selected in mode selection information from among a plurality of different boundary patterns previously associated with different operation modes, as boundaries of a boundary image in the boundary image generation unit 2355. The boundary pattern setting unit 2335 selects, from among a plurality of different boundary patterns previously associated with different combinations of operation modes and pieces of identification information on the ultrasound endoscope 2, a boundary pattern associated with an operation mode selected in mode selection information and the identification information on the ultrasound endoscope 2 acquired by the endoscope information acquisition unit 331, as boundaries of a boundary image in the boundary image generation unit 2355.

The boundary image generation unit 2355 generates a boundary image showing boundaries in a boundary pattern set by the boundary pattern setting unit 2335.

Figure 14:
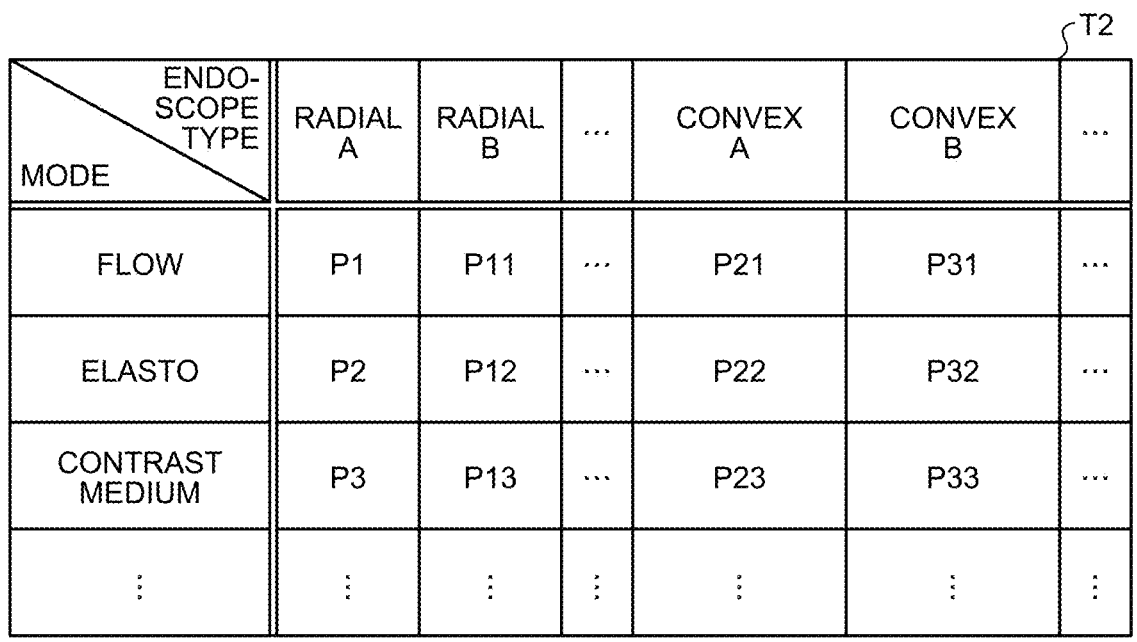
FIG. 14 is a diagram illustrating an example of a boundary pattern table illustrated in FIG. 13.

The storage unit 39 stores a boundary pattern table 2391 showing a plurality of different boundary patterns previously associated with different operation modes. FIG. 14 is a diagram illustrating an example of the boundary pattern table 2391. As in a table T2 exemplified in FIG. 14, in the boundary pattern table 2391, a plurality of boundary pattern numbers P1 to P33 for identifying boundary patterns are previously associated with different combinations of operation modes and pieces of type information on the ultrasound endoscope 2. The boundary pattern numbers P1 to P33 are associated with different boundary patterns corresponding to the numbers. The storage unit 39 stores the different boundary patterns corresponding to the boundary pattern numbers.

Figure 15:
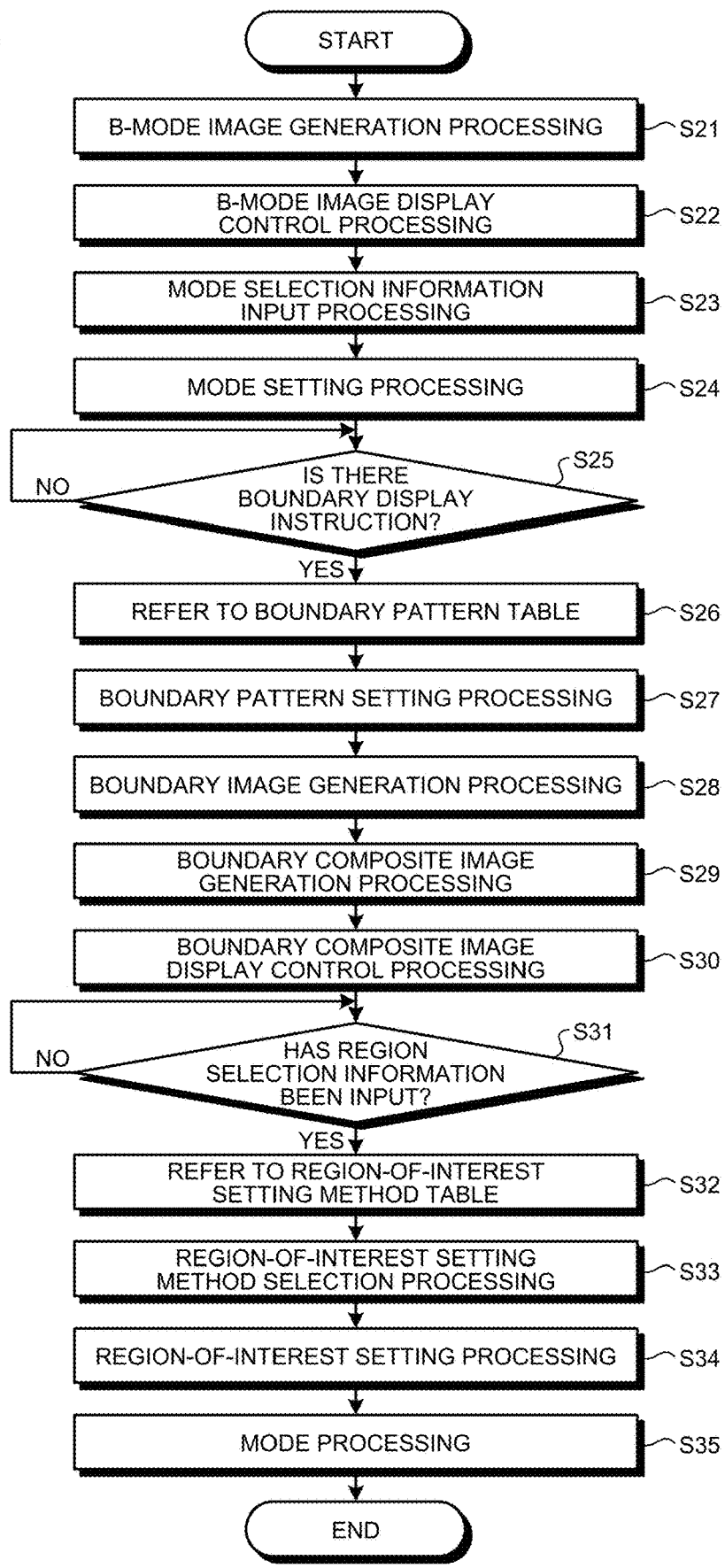
FIG. 15 is a flowchart illustrating a processing procedure for an ultrasound observation apparatus illustrated in FIG. 13 to set a region of interest and generate a composite image for the set region of interest.

FIG. 15 is a flowchart illustrating a processing procedure for the ultrasound observation apparatus 203 to set a region of interest, and generate a composite image for the set region of interest. Steps S21 to S25 illustrated in FIG. 15 are steps S1 to S5 illustrated in FIG. 3. When the control unit 233 determines that there is a boundary display instruction (step S25: Yes), the boundary pattern setting unit 2335 refers to the boundary pattern table 2391 stored in the storage unit 39 (step S26). The boundary pattern setting unit 2335 performs boundary pattern setting processing to select, from among the boundary pattern numbers in the boundary pattern table 2391 referred to, a boundary pattern number associated with an operation mode selected in mode selection information and the identification information on the ultrasound endoscope 2 acquired by the endoscope information acquisition unit 331, and set the boundary pattern corresponding to the selected boundary pattern number as boundaries of a boundary image in the boundary image generation unit 2355 (step S27). As a result, the boundary image generation unit 2355 performs boundary image generation processing to read the boundary pattern corresponding to the boundary pattern number set by the boundary pattern setting unit 2335 from the storage unit 39, and generate a boundary image showing boundaries in the read boundary pattern (step S28). Steps S29 to S35 illustrated in FIG. 15 are steps S7 to S13 illustrated in FIG. 3.

Next, boundary patterns set in the boundary pattern setting processing illustrated in FIG. 15 will be described. FIGS. 16 to 20 are diagrams for explaining an example of the boundary patterns.

Figure 16:
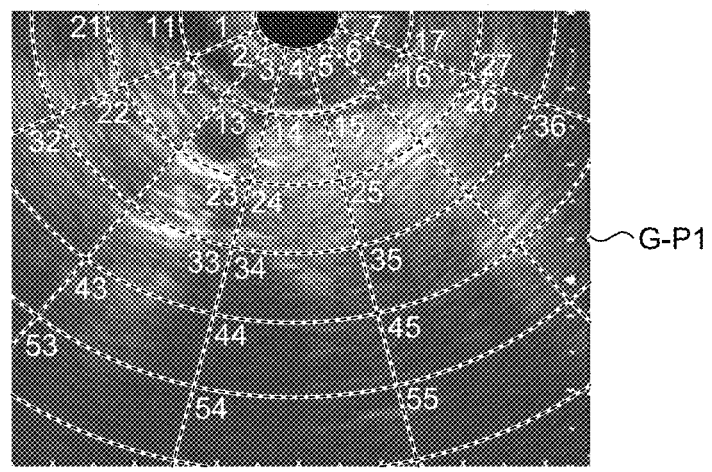
FIG. 16 is a diagram for explaining an example of a boundary pattern.
Figure 17:
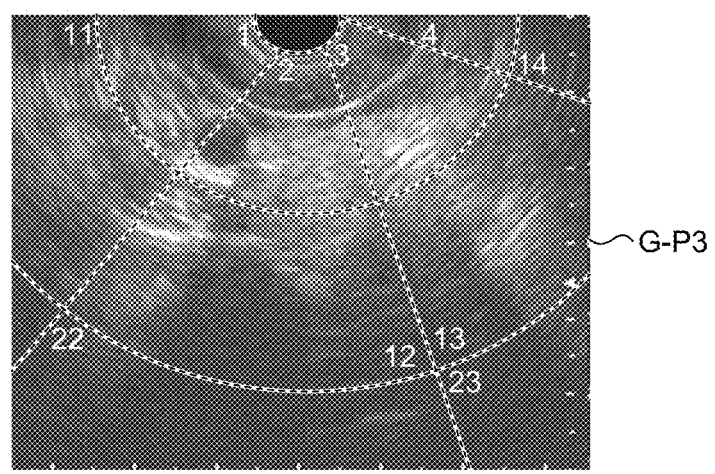
FIG. 17 is a diagram for explaining an example of a boundary pattern.
Figure 18:
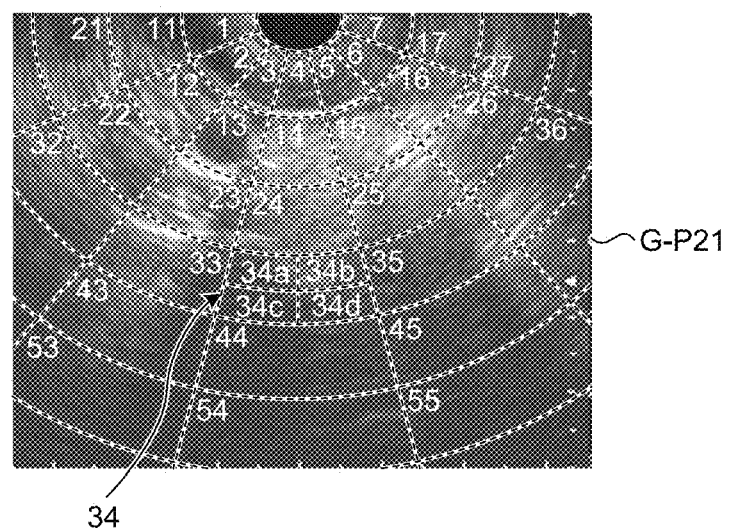
FIG. 18 is a diagram for explaining an example of a boundary pattern.

For example, the boundary pattern corresponding to the boundary pattern number P1 is a default boundary pattern, in which, as illustrated in a boundary composite image G-P1 in FIG. 16, six straight lines extending radially from a top portion of the image and seven arcs intersecting with the straight lines indicate the boundaries of regions, dividing the B-mode image into 32 regions.

When the ultrasound endoscope 2 connected to the ultrasound observation apparatus 203 is the radial A type, and the contrast medium-mode is selected as the operation mode, the boundary pattern setting unit 2335 selects the boundary pattern corresponding to the boundary pattern number P3 from among the plurality of boundary pattern numbers P1 to P33 presented in the table T2 in FIG. 14. The boundary pattern corresponding to the boundary pattern number P3 is a pattern in which, as illustrated in a boundary composite image G-P3 in FIG. 17, for example, boundaries are presented such that regions larger than the regions divided by the default boundary pattern are arranged. In the boundary pattern corresponding to the boundary pattern number P3, three straight lines extending radially from a top portion of the image and three arcs intersecting with the straight lines indicate the boundaries of the regions, dividing the B-mode image into ten regions. The region-of-interest setting method selection unit 333 may set an optimum region-of-interest setting method, according to the boundary pattern set by the boundary pattern setting unit 2335.

When identification information indicating that the ultrasound endoscope 2 is of the convex A type is acquired by the endoscope information acquisition unit 331, the boundary pattern setting unit 2335 sets a boundary pattern in which, among regions divided by a predetermined reference boundary pattern illustrated in the boundary composite image G-P1 in FIG. 16, for example, the interior of the boundaries enclosing a region 34 that may be presumed to be reached by the tip of the puncture needle at the maximum protrusion of the puncture needle is further divided into a plurality of regions. As a result, each of the divided regions 34a to 34d of the region 34 that may be presumed to be reached by the puncture needle may also be selected as a desired region, and the size of a region of interest may be finely adjusted. Specifically, when the ultrasound endoscope 2 connected to the ultrasound observation apparatus 203 is of the convex A type, and the flow-mode is selected as the operation mode, the boundary pattern setting unit 2335 selects the boundary pattern corresponding to the boundary pattern number P21 from among the plurality of boundary pattern numbers P1 to P33 presented in the table T2 in FIG. 14. The boundary pattern corresponding to the boundary pattern number P21 is a pattern in which, as illustrated in a boundary composite image G-P21 in FIG. 18, for example, among the regions divided by the default boundary pattern, broken lines further dividing the interior of the region 34 into four regions are further presented. Identification numbers of "34a to 34d" are assigned to the divided regions of the region 34.

Figure 19:
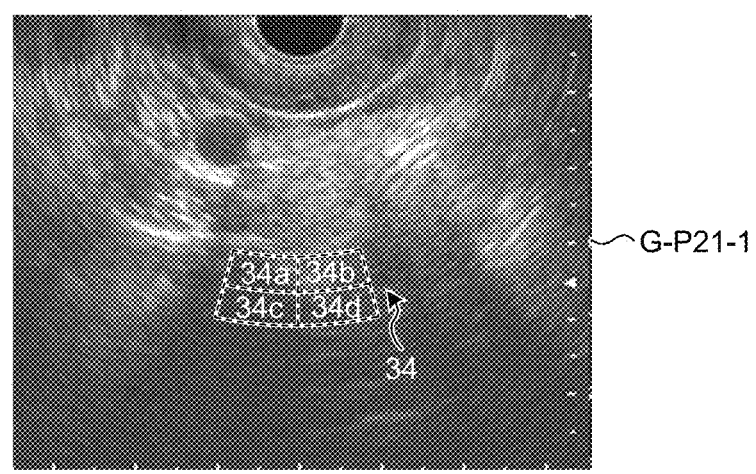
FIG. 19 is a diagram for explaining an example of a boundary pattern.

The boundary pattern corresponding to the boundary pattern number P21 may be a pattern in which, as illustrated in a boundary composite image G-P21-1 in FIG. 19, for example, only the broken lines indicating the boundaries enclosing the region 34 and the broken lines further dividing the interior of the boundaries enclosing the region 34 into four regions are presented.

Figure 20:
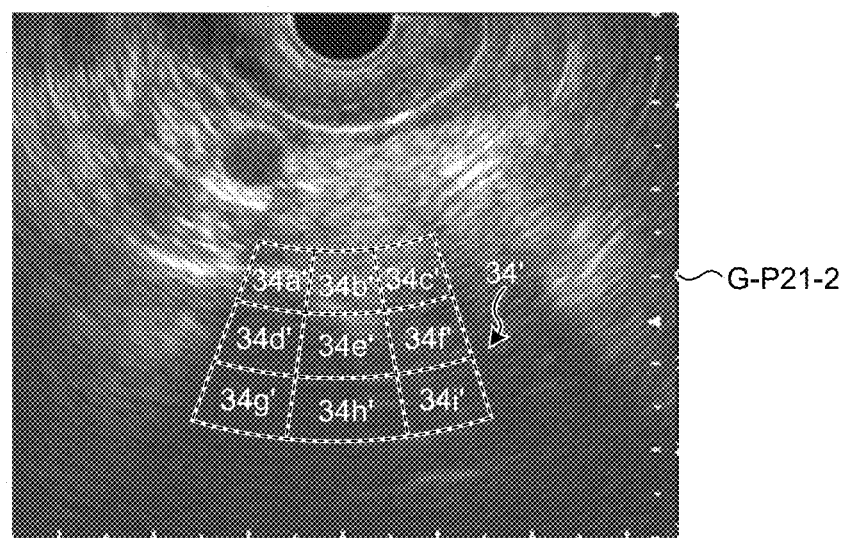
FIG. 20 is a diagram for explaining an example of a boundary pattern.

Alternatively, the boundary pattern corresponding to the boundary pattern number P21 may be a pattern in which, as illustrated in a boundary composite image G-P21-2 in FIG. 20, for example, the boundaries enclosing the region 34 are enlarged at a predetermined magnification, and broken lines further dividing the interior of a region 34' enclosed by the enlarged boundaries into nine regions of regions 34a' to 34i' are presented. In other words, the boundary pattern setting unit 2335 may set a boundary pattern in which, among regions divided by a reference boundary pattern, boundaries enclosing a region that may be presumed to be reached by the tip of the puncture needle are enlarged at a predetermined magnification, and the interior of the enlarged boundaries are further divided into a plurality of regions. As a result, when the ultrasound endoscope 2 is of the convex A type, a region that may be presumed to be reached by the tip of the puncture needle may be strictly selected in region selection information, and a region of interest may be finely adjusted to the optimum one.

As described above, in the second embodiment, a boundary pattern associated with each operation mode and the type and generation of the ultrasound endoscope 2 is set to generate a boundary image. Consequently, according to the second embodiment, the operator may select a region suitable for observation from among divided regions divided in a manner suitable for the operation mode and the type and generation of the ultrasound endoscope 2, and thus may flexibly select a region suitable for the operation mode and the type and generation of the ultrasound endoscope 2, and may obtain a region of interest of an optimum size.

In the first and second embodiments described above, the description has been made on the assumption that the flow-mode, the elasto-mode, or the contrast medium-mode is set as the operation mode. The present disclosure is not limited to this, and the operation mode may be, for example, a distance measurement mode, an area measurement mode, a pulse Doppler Mode, a contrast harmonic mode, or a tissue harmonic mode.

Further, the region-of-interest setting unit 334 may analyze an image in a region of interest, and correct the region of interest to further optimize the region of interest. In this case, the region-of-interest setting unit 334 performs image analysis by acquiring histogram (noise) distribution, contours, flow rate distribution, or strain amount distribution in the image inside the region of interest. In this case, a region unnecessary as a region to be subjected to mode processing may be deleted, and the processing speed of each operation mode may be increased, improving the frame rate. In the case of the elasto-mode, measurement accuracy (display accuracy) may be enhanced.

In the first and second embodiments, when the operator changes the operation mode, the ultrasound observation apparatus 3 or 203 executes the processing steps starting from step S1 in FIG. 3 or step S21 in FIG. 15 again. In the first embodiment, when the operator utters "boundary" in and after step S9 in FIG. 3, the process may return to step S6 to generate a boundary image again and generate and display a boundary composite image superimposed on the B-mode image. This is the same in the second embodiment. If the operator utters "boundary" in and after step S31 illustrated in FIG. 15, the process returns to step S26. If the operator utters a new region number during the processing in step S13 in FIG. 3 or step S35 in FIG. 15, the process may return to step S9 in FIG. 3 or step S31 in FIG. 15 to perform the subsequent processing. The first and second embodiments have presented an example in which division into regions is performed by enclosing regions on a B-mode image with boundary lines. Alternatively, division into regions may be performed by color-coding regions differently.

In the first and second embodiments described above, the description has been made on the assumption that the ultrasound observation apparatus 3 or 203 and the display device 4 are provided as separate bodies. Alternatively, the ultrasound observation apparatus 3 or 203 and the display device 4 may be integrated.

An operation program for the processing steps executed in the components of the ultrasound observation apparatus 3 or 203 according to the present embodiments may be configured to be provided in a file in a installable format or in an executable format recorded in a computer-readable recording medium such as a CD-ROM, a flexible disk, a CD-R, or a DVD, or may be configured to be stored in a computer connected to a network such as the Internet and provided by being downloaded via the network. Alternatively, the operation program may be configured to be provided or distributed via a network such as the Internet.

In the first and second embodiments described above, the description has been made with an observation target being living tissue as an example. The embodiments are also applicable to an industrial endoscope for observing the characteristics of materials. The observation apparatus according to the present disclosure is applicable both inside and outside the body. Instead of ultrasound waves, the observation apparatus may emit infrared rays or the like to transmit and receive signals of an observation target.

The present disclosure achieves the effect that a region of interest suitable for each operation mode may be set with a simple operation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation apparatus comprising:
a processor comprising hardware, the processor being configured to:
control an ultrasound endoscope to transmit ultrasound waves to a subject that is an observation target, receive the ultrasound waves reflected by the subject, acquire ultrasound signal based on the ultrasound waves received, and generate ultrasound images based on the ultrasound signal acquired;
generate a B-mode image in which amplitude of the ultrasound waves reflected is converted into luminance by processing the ultrasound signal and presented in two dimensions;
generate a boundary composite image showing mesh-like boundaries that divide the B-mode image into a plurality of divided regions superimposed on the B-mode image;
receive input of region selection information selecting a desired region in the B-mode image from the plurality of divided regions;
receive input of an operation mode selection information selecting an operation mode for detecting a piece of characteristic biological information from among a plurality of operation modes for detecting a plurality of pieces of characteristic biological information respectively;
select a group of region-of-interest setting methods from among a plurality of groups of region-of-interest setting methods based on the operation mode selected, wherein each of the plurality of groups of region-of-interest setting methods is associated with a different operation mode of the plurality of operation modes;
acquire identification information of the ultrasound endoscope from among a plurality of identification information;
select the region-of-interest setting method associated with the operation mode selected and the identification information of the ultrasound endoscope, from among the group of region-of-interest setting methods selected;
set a range of a region of interest within each of the ultrasound images to be subjected to processing in the operation mode selected, the range of the region of interest including one or more of a portion of the desired region, the desired region and other divided regions of the plurality of regions, based on the desired region selected in the B-mode image and the region-of-interest setting method from the group of region-of-interest setting methods selected; and
generate a mode composite image in which an operation mode image presented in two dimensions additional information obtained by performing processing suitable for the operation mode selected in accordance with the input on the region of interest is superimposed on the B-mode image generated,
wherein the plurality of operation modes comprises a flow-mode, an elasto-mode, and a contrast medium-mode, and
wherein the processor is configured to:
in response to the flow-mode being received as the operation mode selection information, and a first region and a second region being selected in accordance with the input of the region selection information received, set the range of the region of interest to comprise the first region, the second region, and a region through which, among acoustic rays passing through the first region and the second region, acoustic rays of depths between a shallowest depth and a deepest depth pass;
in response to the elasto-mode being selected, and a third region and a fourth region being selected in the region selection information received, set the range of the region of interest to comprise a region with vertices thereof at midpoints of diagonal lines of the third region and the fourth region, and of regions through which, among acoustic rays passing through the third region and the fourth region, acoustic rays of depths between the shallowest depth and the deepest depth pass, in the regions;
in response to the contrast medium-mode being selected, set the range of the region of interest to comprise the desired region and a region in a predetermined range around the desired region; and
in response to the identification information indicating that the ultrasound endoscope is of a convex type capable of protruding a puncture needle from a distal end opening is acquired, set the range of the region of interest to comprise the desired region and a region containing a path along which a tip of the puncture needle passes are contained,
wherein the shallowest depth refers to a state where a distance from a transducer to the first and the second regions in the ultrasound image is closest, and the deepest depth refers to a state where the distance from the transducer to the first and the second regions in the ultrasound image is farthest.

2. The ultrasound observation apparatus according to claim 1,
wherein the processor is configured to receive input of the region selection information by voice.

3. The ultrasound observation apparatus according to claim 1,
wherein the processor is configured to generate the boundary composite image showing the mesh-like boundaries and region identification information for identifying the divided regions.

4. The ultrasound observation apparatus according to claim 1,
wherein the processor is configured to control a display to display the mode composite image and the boundary composite image.

5. The ultrasound observation apparatus according to claim 1,
wherein the processor is configured to:
set a boundary pattern of the mesh-like boundaries associated with the operation mode selected from among a plurality of different boundary patterns associated with the plurality of operation modes, respectively; and
generate the boundary composite image showing the mesh-like boundaries having the boundary pattern sets superimposed on the B-mode image.

6. The ultrasound observation apparatus according to claim 5,
wherein the operation mode is a contrast medium-mode, and
wherein in response to the contrast medium-mode being selected, set the boundary pattern of the mesh-like boundaries such that regions divided by the mesh-like boundaries are larger than regions divided by boundaries of a predetermined reference boundary pattern.

7. The ultrasound observation apparatus according to claim 1,
wherein the processor is configured to:
set a boundary pattern of the mesh-like boundaries based on the operation mode selected and the identification information of the ultrasound endoscope acquired from among a plurality of different boundary patterns associated with different combinations of the plurality of operation modes and a plurality of identification information; and
generate the boundary composite image showing the mesh-like boundaries having the boundary pattern set.

8. The ultrasound observation apparatus according to claim 7,
wherein the processor is configured to, in response to the identification information indicating that the ultrasound endoscope is of a convex type capable of protruding a puncture needle from a distal end opening, set the boundary pattern of the mesh-like boundaries such that boundaries enclosing a region that may be presumed to be reached by a tip of the puncture needle among regions divided by a reference boundary pattern are enlarged at a magnification, and an interior of the enlarged boundaries is further divided into a plurality of regions.

9. An operation method comprising:
controlling an ultrasound endoscope to transmit ultrasound waves to a subject that is an observation target, receiving the ultrasound waves reflected by the subject, acquiring ultrasound signal based on the ultrasound waves received, and generating ultrasound images based on the ultrasound signal acquired;
generating a B-mode image in which amplitude of the ultrasound waves reflected is converted into luminance by processing the ultrasound signal, and presented in two dimensions;
generating a boundary composite image showing mesh-like boundaries that divide the B-mode image into a plurality of divided regions superimposed on the B-mode image;
receiving input of region selection information selecting a desired region in the B-mode image from the plurality of divided regions;
receiving input of an operation mode selection information selecting an operation mode for detecting a piece of characteristic biological information from among a plurality of operation modes for detecting a plurality of pieces of characteristic biological information respectively;
selecting a group of region-of-interest setting methods from among a plurality of groups of region-of-interest setting methods based on the operation mode selected, wherein each of the plurality of groups of region-of-interest setting methods is associated with a different operation mode of the plurality of operation modes;
acquiring identification information of the ultrasound endoscope from among a plurality of identification information;
selecting the region-of-interest setting method associated with the operation mode selected and the identification information of the ultrasound endoscope, from among the group of region-of-interest setting methods selected;
setting a range of a region of interest within each of the ultrasound images to be subjected to processing in the operation mode selected, the range of the region of interest including one or more of a portion of the desired region, the desired region and other divided regions of the plurality of regions, based on the desired region selected in the B-mode image and the region-of-interest setting method from the group of region-of-interest setting methods selected; and
generating a mode composite image in which an operation mode image presented in two dimensions additional information obtained by performing processing suitable for the operation mode selected in accordance with the input on the region of interest is superimposed on the B-mode image generated,
wherein the plurality of operation modes comprises a flow-mode, an elasto-mode, and a contrast medium-mode, and
wherein the operation method comprises:
in response to the flow-mode being received as the operation mode selection information, and a first region and a second region being selected in accordance with the input of the region selection information received, setting the range of the region of interest to comprise the first region, the second region, and a region through which, among acoustic rays passing through the first region and the second region, acoustic rays of depths between a shallowest depth and a deepest depth pass;

in response to the elasto-mode being selected, and a third region and a fourth region being selected in the region selection information received, setting the range of the region of interest to comprise a region with vertices thereof at midpoints of diagonal lines of the third region and the fourth region, and of regions through which, among acoustic rays passing through the third region and the fourth region, acoustic rays of depths between the shallowest depth and the deepest depth pass, in the regions;

in response to the contrast medium-mode being selected, setting the range of the region of interest to comprise the desired region and a region in a predetermined range around the desired region; and in response to the identification information indicating that the ultrasound endoscope is of a convex type capable of protruding a puncture needle from a distal end opening is acquired, setting the range of the region of interest to comprise the desired region and a region containing a path along which a tip of the puncture needle passes are contained, wherein the shallowest depth refers to a state where a distance from a transducer to the first and the second regions in the ultrasound image is closest, and the deepest depth refers to a state where the distance from the transducer to the first and the second regions in the ultrasound image is farthest.

10. A non-transitory computer-readable recording medium with an executable program stored thereon, the program causing a processor to at least execute:

controlling an ultrasound endoscope to transmit ultrasound waves to a subject that is an observation target, receiving the ultrasound waves reflected by the subject, acquiring ultrasound signal based on the ultrasound waves received, and generating ultrasound images based on the ultrasound signal acquired;

generating a B-mode image in which amplitude of the ultrasound waves reflected is converted into luminance by processing the ultrasound signal, and presented in two dimensions;

generating a boundary composite image showing mesh-like boundaries that divide the B-mode image into a plurality of divided regions superimposed on the B-mode image;

receiving input of region selection information selecting a desired region in the B-mode image from the plurality of divided regions;

receiving input of an operation mode selection information selecting an operation mode for detecting a piece of characteristic biological information from among a plurality of operation modes for detecting a plurality of pieces of characteristic biological information respectively;

selecting a group of region-of-interest setting methods from among a plurality of groups of region-of-interest setting methods based on the operation mode selected, wherein each of the plurality of groups of region-of-interest setting methods is associated with a different operation mode of the plurality of operation modes;

acquiring identification information of the ultrasound endoscope from among a plurality of identification information;

selecting the region-of-interest setting method associated with the operation mode selected and the identification information of the ultrasound endoscope, from among the group of region-of-interest setting methods selected;

setting a range of a region of interest within each of the ultrasound images to be subjected to processing in the operation mode selected, the range of the region of interest including one or more of a portion of the desired region, the desired region and other divided regions of the plurality of regions, based on the desired region selected in the B-mode image and the region-of-interest setting method from the group of region-of-interest setting methods selected; and generating a mode composite image in which an operation mode image presented in two dimensions additional information obtained by performing processing suitable for the operation mode selected in accordance with the input on the region of interest is superimposed on the B- mode image generated, wherein the plurality of operation modes comprises a flow-mode, an elasto-mode, and a contrast medium-mode, and wherein the program causes the processor to execute:

in response to the flow-mode being received as the operation mode selection information, and a first region and a second region being selected in accordance with the input of the region selection information received, setting the range of the region of interest to comprise the first region, the second region, and a region through which, among acoustic rays passing through the first region and the second region, acoustic rays of depths between a shallowest depth and a deepest depth pass;

in response to the elasto-mode being selected, and a third region and a fourth region being selected in the region selection information received, setting the range of the region of interest to comprise a region with vertices thereof at midpoints of diagonal lines of the third region and the fourth region, and of regions through which, among acoustic rays passing through the third region and the fourth region, acoustic rays of depths between the shallowest depth and the deepest depth pass, in the regions;

in response to the contrast medium-mode being selected, setting the range of the region of interest to comprise the desired region and a region in a predetermined range around the desired region; and in response to the identification information indicating that the ultrasound endoscope is of a convex type capable of protruding a puncture needle from a distal end opening is acquired, setting the range of the region of interest to comprise the desired region and a region containing a path along which a tip of the puncture needle passes are contained, wherein the shallowest depth refers to a state where a distance from a transducer to the first and the second regions in the ultrasound image is closest, and the deepest depth refers to a state where the distance from the transducer to the first and the second regions in the ultrasound image is farthest.

* * * * *